(12) United States Patent
Yamamoto et al.

(10) Patent No.: US 11,000,572 B2
(45) Date of Patent: *May 11, 2021

(54) COMPOSITION HAVING TISSUE-REPAIRING ACTIVITY, AND USE THEREFOR

(71) Applicant: TOKUSHIMA UNIVERSITY, Tokushima (JP)

(72) Inventors: Akihito Yamamoto, Nagoya (JP); Minoru Ueda, Nagoya (JP); Kohki Matsubara, Nagoya (JP); Akio Suzumura, Nagoya (JP); Koichi Furukawa, Nagoya (JP); Yoshihiro Matsushita, Nagoya (JP); Hirotaka Wakayama, Nagoya (JP); Nobunori Takahashi, Nagoya (JP); Shin Tsunekawa, Nagoya (JP); Takako Izumoto, Nagoya (JP)

(73) Assignee: TOKUSHIMA UNIVERSITY, Tokushima (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/671,497

(22) Filed: Nov. 1, 2019

(65) Prior Publication Data
US 2020/0129591 A1 Apr. 30, 2020

Related U.S. Application Data

(60) Continuation of application No. 15/938,839, filed on Mar. 28, 2018, now Pat. No. 10,507,230, which is a division of application No. 14/654,624, filed as application No. PCT/JP2013/084523 on Dec. 24, 2013, now Pat. No. 9,962,428.

(30) Foreign Application Priority Data

Dec. 21, 2012 (JP) ................................. 2012-280022

(51) Int. Cl.
| | | |
|---|---|---|
| *A61K 38/19* | (2006.01) | |
| *C12N 5/0786* | (2010.01) | |
| *A61K 45/06* | (2006.01) | |
| *A61K 31/737* | (2006.01) | |
| *A61K 38/17* | (2006.01) | |

(52) U.S. Cl.
CPC .......... *A61K 38/195* (2013.01); *A61K 31/737* (2013.01); *A61K 38/178* (2013.01); *A61K 45/06* (2013.01); *C12N 5/0645* (2013.01); *C12N 2501/21* (2013.01); *C12N 2501/59* (2013.01); *C12N 2501/90* (2013.01)

(58) Field of Classification Search
CPC .............. A61K 38/195; C12N 5/0645
See application file for complete search history.

(56) References Cited

U.S. PATENT DOCUMENTS

| 6,989,435 B2* | 1/2006 | Grainger | A61P 3/14 530/328 |
|---|---|---|---|
| 2003/0036631 A1* | 2/2003 | Longphre | C07K 14/705 530/350 |
| 2004/0176309 A1* | 9/2004 | Keim | A61P 37/00 514/23 |
| 2007/0065415 A1* | 3/2007 | Kleinsek | A61K 35/12 424/93.7 |
| 2007/0244038 A1* | 10/2007 | Varki | A61K 31/739 424/184.1 |
| 2009/0238837 A1* | 9/2009 | Paulson | A61K 31/739 424/172.1 |
| 2010/0166733 A1 | 7/2010 | Levin et al. | |
| 2011/0064746 A1 | 3/2011 | Liu et al. | |
| 2012/0201819 A1 | 8/2012 | Liu et al. | |
| 2013/0195991 A1 | 8/2013 | Ueda et al. | |

FOREIGN PATENT DOCUMENTS

| JP | H07-507567 A | 8/1995 |
|---|---|---|
| JP | 2001-352977 A | 12/2001 |
| JP | 2002-532556 A | 10/2002 |
| JP | 2008-094746 A | 4/2008 |
| WO | 94/08606 A1 | 4/1994 |
| WO | 00/37096 A1 | 6/2000 |
| WO | 2011/118795 A1 | 9/2011 |

OTHER PUBLICATIONS

Von Gunten et al., 2005, Siglec-9 transduces apoptotic and nonapoptotic death signals into neutrophils depending on the proinflammatory cytokine environment, Blood, 106(4): 1423-1431.*
O'Reilly et al., 2009, Siglecs as targets for therapy in immune cell mediated disease, Trends Pharmacol Sci, 30(5): 240-248.*
David et al., "Repertoire of Microglial and Macrophage Responses after Spinal Cord Injury," Nature Reviews, Neuroscience, Jul. 2011, vol. 12, No. 7, pp. 388-399.
Popovich et al., "Can the Immune System be Harnessed to Repair the CNS?" Natures Reviews, Neuroscience, Jun. 2008, vol. 9, No. 6, pp. 481-493.
Ando et al., "Jiko Soshiki Shinseik Saisei ni Okeru CCR2 Izongata—Seitainai Kansaibo Shuseki no Yakuwari," Regenerative Medicine, 2011, vol. 10, p. 212.
Szymczak et al., "The CCL7-CCL2-CCR2 Axis Regulates IL-4 Production in Lungs and Fungal Immunity," J Immunol, 2009, vol. 183, No. 3, pp. 1964-1974.

(Continued)

*Primary Examiner* — Amber D Steele
(74) *Attorney, Agent, or Firm* — Oliff PLC

(57) ABSTRACT

A composition having tissue repair activity, which is capable of promoting reactions associated with tissue repair, contains at least one selected from the group consisting of a first component that is a protein having a monocyte chemotactic protein-1 (MCP-1) activity, a second component that is a protein having the extracellular domain activity of sialic acid-binding immunoglobulin-type lectin-9 (Siglec-9), and a third component that is at least one of chondroitin sulfate and chondroitin sulfate proteoglycan.

19 Claims, 24 Drawing Sheets
Specification includes a Sequence Listing.

(56) References Cited

OTHER PUBLICATIONS

Muzzarelli et al., "Chitosan, Hyaluronan and Chondroitin Sulfate in Tissue Engineering for Cartilage Regeneration: A Review," Carbohydrate Polymers, Jul. 2012, vol. 89, No. 3, pp. 723-739.
Tsuji "Physical Properties and Tissue Response of Canal Sealer Pastes Containing Tetracalcium Phosphate-Chondroitin Sulfate," Nihon Shika Hozongaku Zasshi, 1993, vol. 36, No. 3, pp. 31-32. Introduction to the Glyoscience Dai 5 Kai—Saibogain Matrix 2—Kenko na Karada o Sasaeru Urakata—Chondroitin Ryusan, Seikagaku Corp., 2007—Retrieved from the Internet <<http://www.glycoforum.gr.jp/glyco/05.html>>.
Zhang et al., "Siglec-9, a Novel Sialic Acid Binding Member of the Immunoglobulin Superfamily Expressed Broadly on Human Blood Leukocytes," The Journal of Biological Chemistry, 2000, vol. 275, No. 29, pp. 22121-22126.
Ando et al., "Stem Cell-Conditioned Medium Accelerates Distraction Osteogenesis through Multiple Regenerative Mechanisms," Bone, 2014, vol. 61, pp. 82-90.
Ando et al., "Siglec-9 Enhances IL-10 Production in Macrophages via Tyrosine-Based Motifs," Biochemical and Biophysical Research Communications, 2008, vol. 369, No. 3, pp. 878-883.
Park-Min et al., "Regulation of Macrophage Phenotype by Long-Term Exposure to IL-10," Immunobiology, 2005, vol. 210, pp. 77-86.
Apr. 1, 2014 International Search Report issued in International Patent Application No. PCT/JP2013/084523.
Apr. 1, 2014 Written Opinion issued in International Patent Application No. PCT/JP2013/084523.
Feb. 3, 2015 International Preliminary Report on Patentability issued in International Patent Application No. PCT/JP2013/084523.
Aug. 16, 2016 Partial Supplementary Search Report issued in European Patent Application No. 13864639.3.
Smith, Matthew J. et al.: "Feasibility of Electrospun Polydioxanone—Monocyte Chemotactic Protein-1 (MCP-1) Hybrid Scaffolds as Potential Cellular Homing Devices," Journal of Engineered Fibers and Fabrics, vol. 5, No. 4. Jan. 1, 2010, pp. 1-9.
Laabs, T. et al., "Chondroitin sulfate proteoglycans in neural development and regeneration," Current Opinion in Neurobiology, London, GB, vol. 15, No. 1, Feb. 1, 2005, pp. 116-120.
Varki A. et al., "Siglecs—the major subfamily of I-type lectins," Glycobiology, Oxford University Press, US, vol. 16, No. 1, Jul. 1, 2005, pp. 1R-27R.
Pillai, Shiv et al. "Siglecs and Immune Regulation," Annual Review of Immunology., vol. 30, No. 1, Apr. 23, 2012, pp. 357-392.
Sakai, Kyoshi et al. "Human dental pulp-driven stem cells promote locomotor recovery after complete transection of the rat spinal cord by multiple neuro-regenerative mechanisms," Journal of Clinical Investigation, Jan. 1, 2012, pp. 80-90.
Senda, Motohiro et al. "Identification and expression of a sialyltransferase responsible for the synthesis of disialylgalactosylgloboside in normal and malignant kidney cells: downregulation of ST6GalNAc VI in renal cancers," Biochemical Journal vol. 402, No. 3, Mar. 15, 2007, pp. 459-470.
Maximilien Bencze et al.: "Proinflammatory Macrophages Enhances the Regenerative Capacity of Human Myoblasts by Modifying Their Kinetics of Proliferation and Differentiation", Molecular Therapy, vol. 20, No. 11, Nov. 16, 2012, pp. 2168-2179.
Yamamoto, Akihito et al. "Multifaceted neuro-regenerative activities of human dental pulp stem cells for functional recovery after spinal cord injury," Neuroscience Research., vol. 78, Jan. 1, 2014, pp. 16-20.
Matsubara, K. et al.: "Secreted Ectodomain of Sialic Acid-Binding Ig-Like Lectin-9 and Monocyte Chemoattractant Protein-1 Promote Recovery after Rat Spinal Cord Injury by Altering Macrophage Polarity," Journal of Neuroscience, vol. 35, No. 6, Feb. 11, 2015, pp. 2452-2464.
Dec. 22, 2016 Office Action issued in U.S. Appl. No. 14/654,624.
Nov. 24, 2016 European Search Report issued in European Patent Application No. 13864639.3.
Jul. 17, 2017 Office Action Issued in U.S. Appl. No. 14/654,624.
Nath et al., 1995, The Amino-terminal Immunoglobulin-like Domain of Sialoadhesin Contains the Sialic Acid Binding Site, The Journal of Biological Chemistry, 270(440: 26184-26191.
Angata et al., 2000, Cloning, Characterization, and Phylogenetic Analysis of Siglec-9, a New Member of the CD33-related Group of Siglecs, The Journal of Biological Chemistry, 276(29):22127-22135.
Aug. 8, 2017 Office Action issued in Japanese Patent Application No. 2014-553236.
Feb. 20, 2018 Office Action issued in Japanese Patent Application No. 2014-553236.
May 24, 2019 Office Action issued in U.S. Appl. No. 15/938,839.
McMillan et al., 2008, CD33-related sialic-acid binding immunoglobulin-like lectins in health and science, Carbohydrate Research, 343; 2050-2056.

* cited by examiner

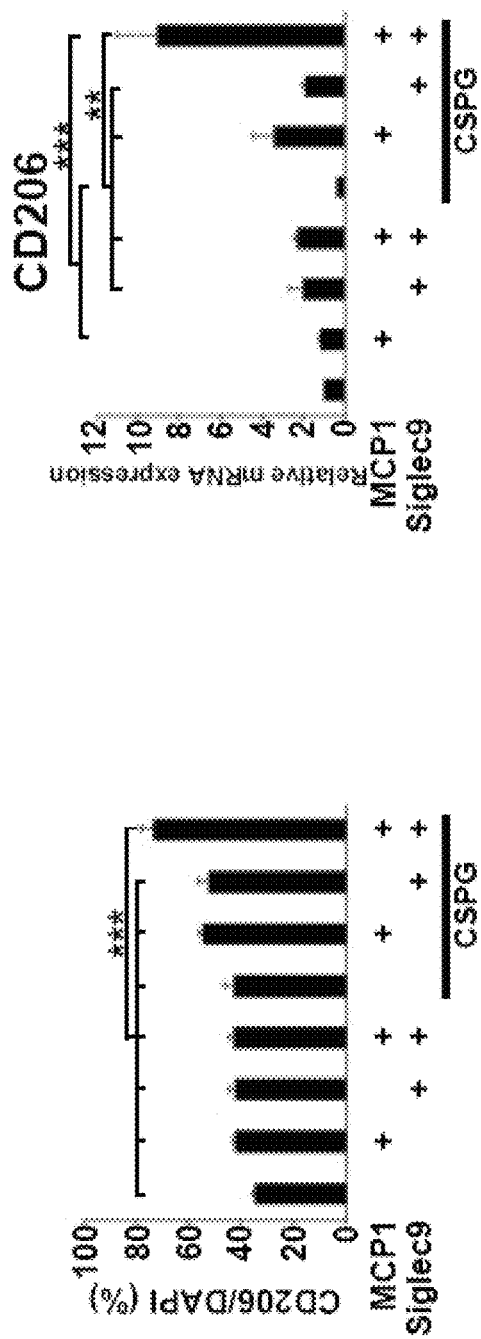
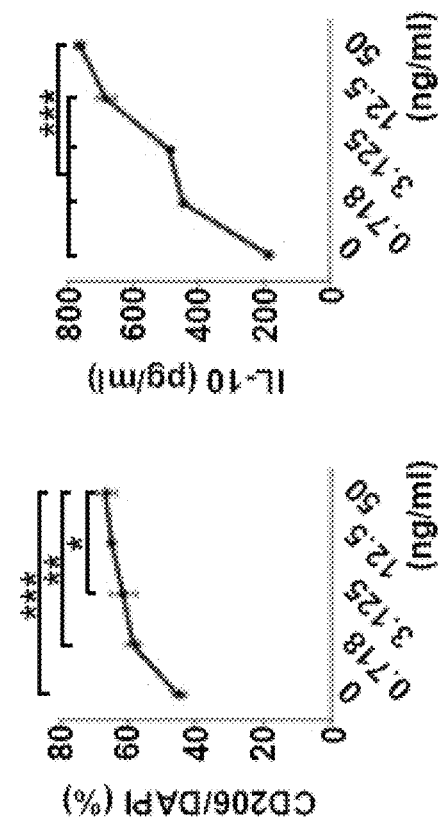
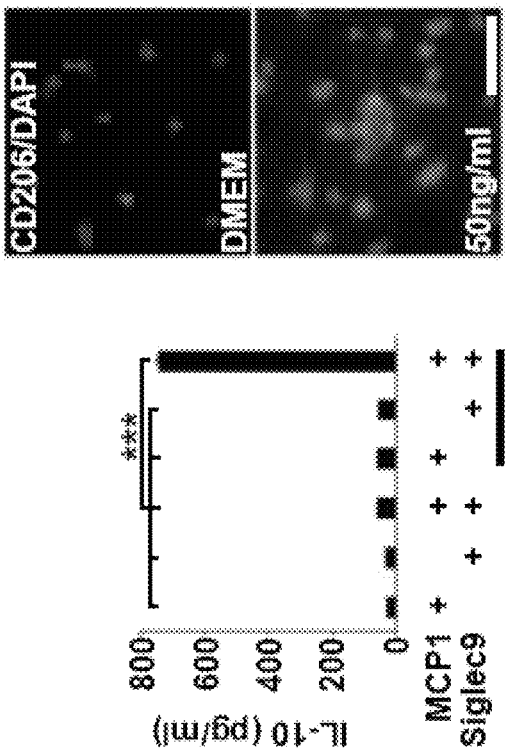
FIG. 6A  FIG. 6B  FIG. 6C  FIG. 6D  FIG. 6E  FIG. 6F

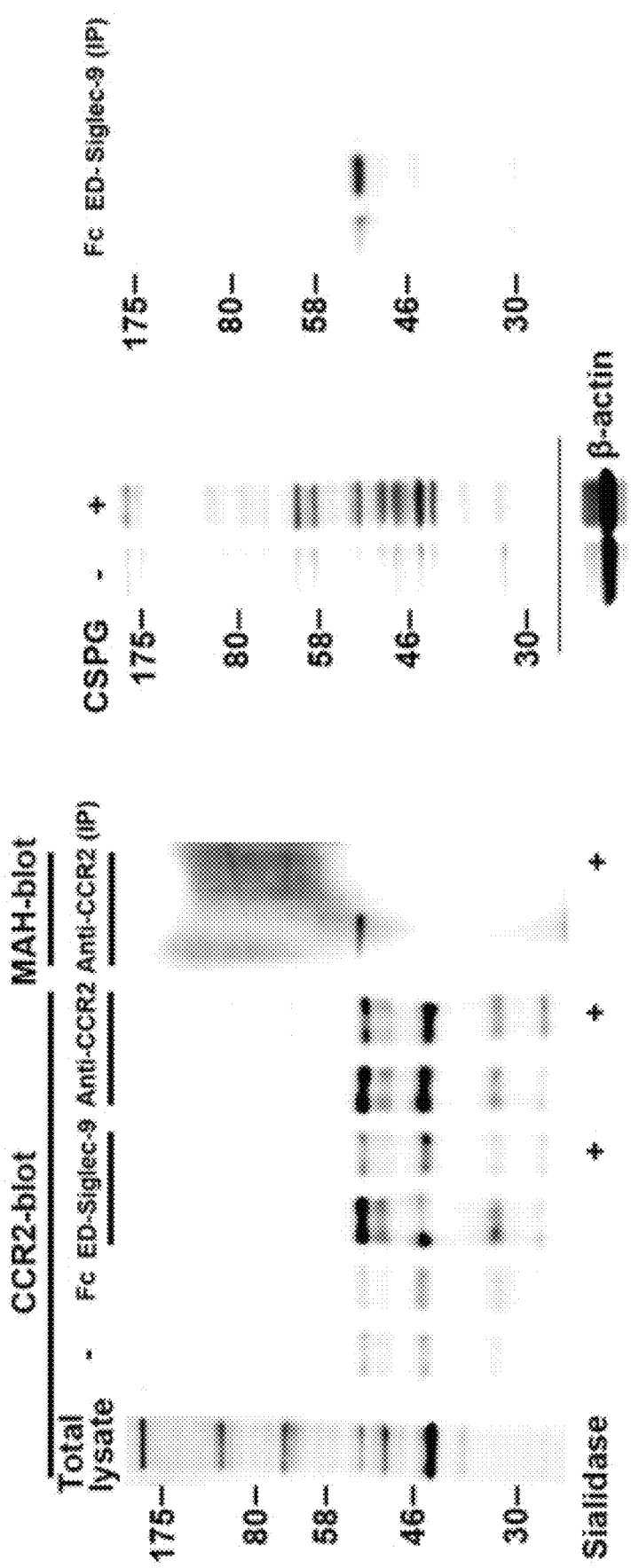

Arthritis score

TNFα conc.(ELISA) in searum

FIG. 21A Arthritis incidence rate
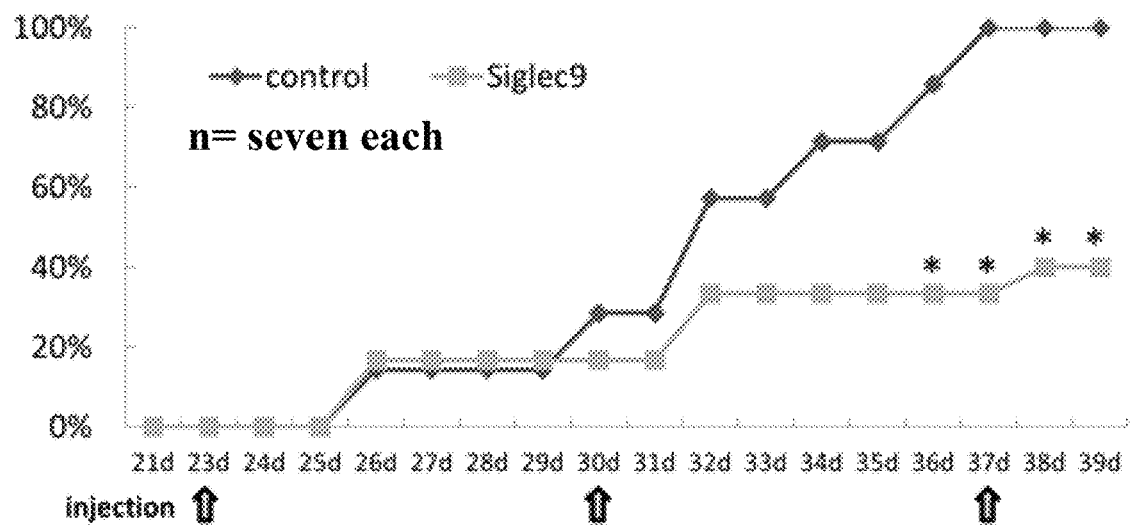
FIG. 21B Arthritis score
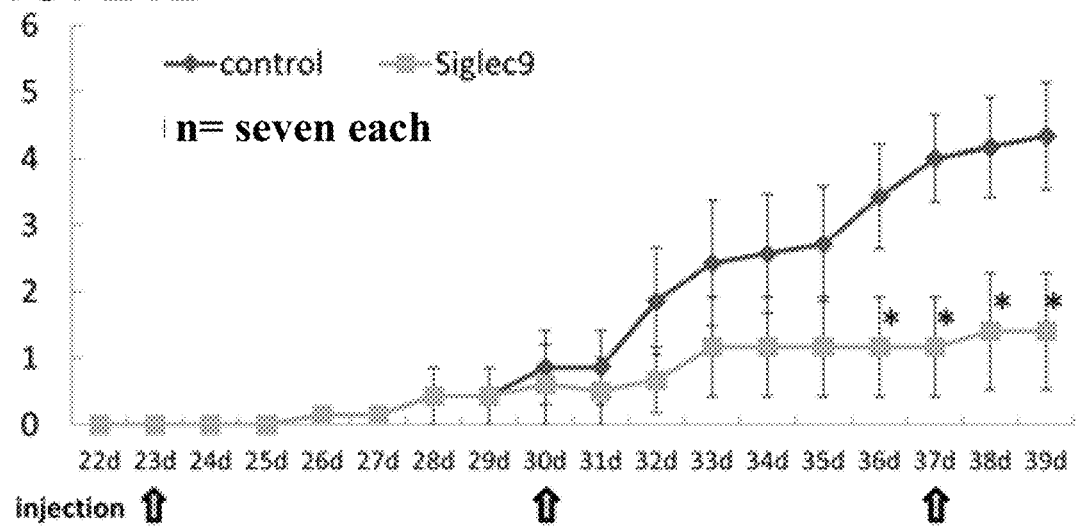
FIG. 21C Relation between TNF α in serum and Arthritis score
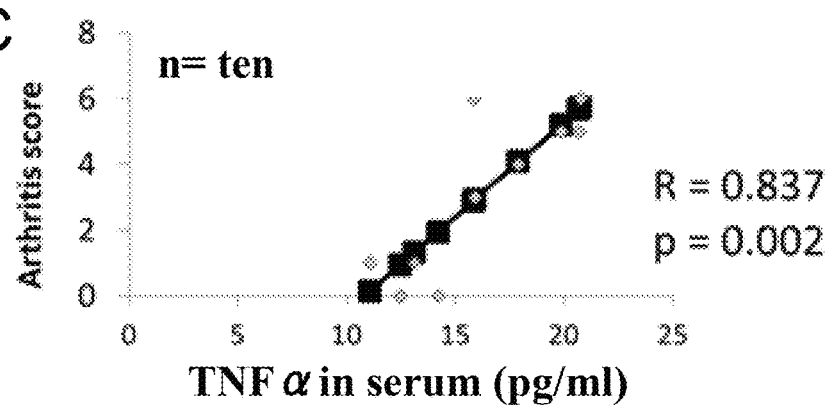

Suppression increased expression of TNF- caused by LPS stimulus by administration of ED-Siglec-9

ED-Siglec-9 administration had no obvious suppression effect on increased expression of MMP-3 mRNA caused by TNF-alfa in FLS

```
SEQUENCE LISTING

<160> NUMBER OF SEQ ID NOS: 37

<210> SEQ ID NO 1
<211> LENGTH: 300
<212> TYPE: DNA
<213> ORGANISM: Homo sapiens

<400> SEQUENCE: 1
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc tatagaagaa tcaccagcag caagtgtccc     180
aaagaagctg tgatcttcaa gaccattgtg gccaaggaga tctgtgctga ccccaagcag     240
aagtgggttc aggattccat ggaccacctg gacaagcaaa cccaaactcc gaagacttga     300

<210> SEQ ID NO 2
<211> LENGTH: 99
<212> TYPE: PRT
<213> ORGANISM: Homo sapiens

<400> SEQUENCE: 2

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30
```

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
 50                  55                  60

Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                 85                  90                  95

Pro Lys Thr

<210> SEQ ID NO 3
<211> LENGTH: 993
<212> TYPE: DNA
<213> ORGANISM: Homo sapiens

<400> SEQUENCE: 3
cagacaagta aactgctgac gatgcagagt tccgtgacgg tgcaggaagg cctgtgtgtc    60
catgtgccct gctccttctc ctaccectcg catggctgga tttaccctgg cccagtagtt   120
catggctact ggttccggga aggggccaat acagaccagg atgctccagt ggccacaaac   180
aacccagctc gggcagtgtg ggaggagact cgggaccgat tccacctcct tggggaccca   240
cataccaaga attgcaccct gagcatcaga gatgccagaa gaagtgatgc ggggagatac   300
ttctttcgta tggagaaagg aagtataaaa tggaattata acatcaccg gctctctgtg    360 aatgtgacag ccttgaccca caggcccaac atcctcatcc caggcaccct ggagtccggc   420 tgccccaga atctgacctg ctctgtgccc tgggcctgtg agcaggggac accccctatg    480
atctcctgga tagggacctc cgtgtccccc ctggacccct ccaccacccg ctcctcggtg   540
ctcaccctca tcccacagcc ccaggaccat ggcaccagcc tcacctgtca ggtgaccttc   600
cctggggcca gcgtgaccac gaacaagacc gtccatctca cgtgtcctac ccgcctcag    660 aacttgacca tgactgtctt ccaaggagac ggcacagtat ccacagtctt gggaaatggc   720
tcatctctgt cactcccaga gggccagtct ctgcacctgg tctgtgcagt tgatgcagtt   780
gacagcaatc cccctgccag gctgagcctg agctggagag gcctgacccct gtgcccctca   840 cagccctcaa acccgggggt gctggagctg ccttgggtgc acctgaggga tgcagctgaa   900
ttcacctgca gagctcagaa ccctctcggc tctcagcagg tctacctgaa cgtctccctg   960
cagagcaaag ccacatcagg agtgactcag ggg                               993

<210> SEQ ID NO 4
<211> LENGTH: 331
<212> TYPE: PRT
<213> ORGANISM: Homo sapiens

<400> SEQUENCE: 4

Gln Thr Ser Lys Leu Leu Thr Met Gln Ser Ser Val Thr Val Gln Glu
 1               5                  10                  15

Gly Leu Cys Val His Val Pro Cys Ser Phe Ser Tyr Pro Ser His Gly
                20                  25                  30

Trp Ile Tyr Pro Gly Pro Val Val His Gly Tyr Trp Phe Arg Glu Gly
                35                  40                  45

Ala Asn Thr Asp Gln Asp Ala Pro Val Ala Thr Asn Asn Pro Ala Arg
 50                  55                  60

Ala Val Trp Glu Glu Thr Arg Asp Arg Phe His Leu Leu Gly Asp Pro
 65                  70                  75                  80

```
His Thr Lys Asn Cys Thr Leu Ser Ile Arg Asp Ala Arg Arg Ser Asp
                 85                  90                  95

Ala Gly Arg Tyr Phe Phe Arg Met Glu Lys Gly Ser Ile Lys Trp Asn
            100                 105                 110

Tyr Lys His His Arg Leu Ser Val Asn Val Thr Ala Leu Thr His Arg
            115                 120                 125

Pro Asn Ile Leu Ile Pro Gly Thr Leu Glu Ser Gly Cys Pro Gln Asn
            130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
            195                 200                 205

Lys Thr Val His Leu Asn Val Ser Tyr Pro Pro Gln Asn Leu Thr Met
            210                 215                 220

Thr Val Phe Gln Gly Asp Gly Thr Val Ser Thr Val Leu Gly Asn Gly
225                 230                 235                 240

Ser Ser Leu Ser Leu Pro Glu Gly Gln Ser Leu Arg Leu Val Cys Ala
                245                 250                 255

Val Asp Ala Val Asp Ser Asn Pro Pro Ala Arg Leu Ser Leu Ser Trp
            260                 265                 270

Arg Gly Leu Thr Leu Cys Pro Ser Gln Pro Ser Asn Pro Gly Val Leu
            275                 280                 285

Glu Leu Pro Trp Val His Leu Arg Asp Ala Ala Glu Phe Thr Cys Arg
            290                 295                 300

Ala Gln Asn Pro Leu Gly Ser Gln Gln Val Tyr Leu Asn Val Ser Leu
305                 310                 315                 320

Gln Ser Lys Ala Thr Ser Gly Val Thr Gln Gly
                325                 330

<210> SEQ ID NO 5
<211> LENGTH: 1392
<212> TYPE: DNA
<213> ORGANISM: Homo sapiens

<400> SEQUENCE: 5
atgctgctgc tgctgctgcc cctgctctgg gggagggaga gggcggaagg acagacaagt      60 aaaactgctga cgatgcagag ttccgtgacg gtgcaggaag gcctgtgtgt ccatgtgccc     120
tgctccttct cctaccccte gcatggctgg atttacctg gcccagtagt tcatggctac       180
tggttccggg aagggggccaa tacagaccag gatgctccag tggccacaaa caacccagct    240
cgggcagtgt gggaggagac tcgggaccga ttccacctcc ttggggaccc acataccaag     300
aattgcaccc tgagcatcag agatgccaga gaagtgatg cggggagata cttctttcgt      360
atggagaaag aagtatataaa atggaattat aaacatcacc ggctctctgt gaatgtgaca    420
gccttgaccc acaggcccaa catcctcatc ccaggcaccc tggagtccgg ctgccccag      480 aatctgacct gctctgtgcc ctgggcctgt gagcagggga caccccctat gatctcctgg    540
atagggacct ccgtgtcccc cctggacccc tccaccaccc gctcctcggt gctcaccctc    600
atcccacagc cccaggacca tggcaccagc ctcacctgtc aggtgacctt ccctgggcc    660 agcgtgacca cgaacaagac cgtccatctc aacgtgtcct acccgcctca gaacttgacc   720
```

```
atgactgtct tccaaggaga cggcacagta tccacagtct tgggaaatgg ctcatctctg    780
tcactcccag agggccagtc tctgcgcctg gtctgtgcag ttgatgcagt tgacagcaat    840 cccctgcca ggctgagcct gagctggaga ggcctgaccc tgtgcccctc acagccctca    900
aacccggggg tgctggagct gccttgggtg cacctgaggg atgcagctga attcacctgc    960
agagctcaga accctctcgg ctctcagcag gtctacctga acgtctccct gcagagcaaa   1020
gccacatcag gagtgactca gggggtggtc gggggagctg agccacagc cctggtcttc    1080 ctgtccttct gcgtcatctt cgttgtagtg aggtcctgca ggaagaaatc ggcaaggcca   1140
gcagcgggcg tgggagatac gggcatagag gatgcaaacg ctgtcagggg ttcagcctct   1200 cagggggccccc tgactgaacc ttgggcagaa gacagtcccc cagaccagcc tcccccagct  1260
tctgcccgct cctcagtggg ggaaggagag ctccagtatg catccctcag cttccagatg   1320
gtgaagcctt gggactcgcg gggacaggag gccactgaca ccgagtactc ggagatcaag   1380
atccacagat ga                                                       1392
```

<210> SEQ ID NO 6
<211> LENGTH: 463
<212> TYPE: PRT
<213> ORGANISM: Homo sapiens

<400> SEQUENCE: 6

```
Met Leu Leu Leu Leu Pro Leu Leu Trp Gly Arg Glu Arg Ala Glu
1               5                   10                  15

Gly Gln Thr Ser Lys Leu Leu Thr Met Gln Ser Ser Val Thr Val Gln
            20                  25                  30

Glu Gly Leu Cys Val His Val Pro Cys Ser Phe Ser Tyr Pro Ser His
        35                  40                  45

Gly Trp Ile Tyr Pro Gly Pro Val Val His Gly Tyr Trp Phe Arg Glu
    50                  55                  60

Gly Ala Asn Thr Asp Gln Asp Ala Pro Val Ala Thr Asn Asn Pro Ala
65                  70                  75                  80

Arg Ala Val Trp Glu Glu Thr Arg Asp Arg Phe His Leu Leu Gly Asp
                85                  90                  95

Pro His Thr Lys Asn Cys Thr Leu Ser Ile Arg Asp Ala Arg Arg Ser
            100                 105                 110

Asp Ala Gly Arg Tyr Phe Phe Arg Met Glu Lys Gly Ser Ile Lys Trp
        115                 120                 125

Asn Tyr Lys His His Arg Leu Ser Val Asn Val Thr Ala Leu Thr His
    130                 135                 140

Arg Pro Asn Ile Leu Ile Pro Gly Thr Leu Glu Ser Gly Cys Pro Gln
145                 150                 155                 160

Asn Leu Thr Cys Ser Val Pro Trp Ala Cys Glu Gln Gly Thr Pro Pro
                165                 170                 175

Met Ile Ser Trp Ile Gly Thr Ser Val Ser Pro Leu Asp Pro Ser Thr
            180                 185                 190

Thr Arg Ser Ser Val Leu Thr Leu Ile Pro Gln Pro Gln Asp His Gly
        195                 200                 205

Thr Ser Leu Thr Cys Gln Val Thr Phe Pro Gly Ala Ser Val Thr Thr
    210                 215                 220

Asn Lys Thr Val His Leu Asn Val Ser Tyr Pro Pro Gln Asn Leu Thr
225                 230                 235                 240

Met Thr Val Phe Gln Gly Asp Gly Thr Val Ser Thr Val Leu Gly Asn
                245                 250                 255
```

```
Gly Ser Ser Leu Ser Leu Pro Glu Gly Gln Ser Leu Arg Leu Val Cys
            260                 265                 270

Ala Val Asp Ala Val Asp Ser Asn Pro Pro Ala Arg Leu Ser Leu Ser
        275                 280                 285

Trp Arg Gly Leu Thr Leu Cys Pro Ser Gln Pro Ser Asn Pro Gly Val
290                 295                 300

Leu Glu Leu Pro Trp Val His Leu Arg Asp Ala Ala Glu Phe Thr Cys
305                 310                 315                 320

Arg Ala Gln Asn Pro Leu Gly Ser Gln Gln Val Tyr Leu Asn Val Ser
                325                 330                 335

Leu Gln Ser Lys Ala Thr Ser Gly Val Thr Gln Gly Val Val Gly Gly
            340                 345                 350

Ala Gly Ala Thr Ala Leu Val Phe Leu Ser Phe Cys Val Ile Phe Val
        355                 360                 365

Val Val Arg Ser Cys Arg Lys Lys Ser Ala Arg Pro Ala Ala Gly Val
370                 375                 380

Gly Asp Thr Gly Ile Glu Asp Ala Asn Ala Val Arg Gly Ser Ala Ser
385                 390                 395                 400

Gln Gly Pro Leu Thr Glu Pro Trp Ala Glu Asp Ser Pro Pro Asp Gln
                405                 410                 415

Pro Pro Pro Ala Ser Ala Arg Ser Ser Val Gly Glu Gly Glu Leu Gln
            420                 425                 430

Tyr Ala Ser Leu Ser Phe Gln Met Val Lys Pro Trp Asp Ser Arg Gly
        435                 440                 445

Gln Glu Ala Thr Asp Thr Glu Tyr Ser Glu Ile Lys Ile His Arg
    450                 455                 460

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
aactttggca tcgtggaagg                                              20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
cggatacatt gggggtagga                                              20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
ttgccttctt gggactgatg                                              20
```

-continued

```
<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
actggtctgt tgtgggtggt                                              20

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
caggatgagg acccaagcac                                              20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
tcagacagca cgaggcattt                                              20

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
ctcgagtgac aagcccgtag                                              20

<210> SEQ ID NO 14
<211> LENGTH: 23
<212> TYPE: DNA
<213> ORGANISM: Artificial
<220> FEATURE:
<223> OTHER INFORMATION: Primer

<400> SEQUENCE: 14
ccttgaagag aacctgggag tag                                          23

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
ggcaggatga gaagctgagg                                              20

<210> SEQ ID NO 16
<211> LENGTH: 20
<212> TYPE: DNA
<213> ORGANISM: Artificial
<220> FEATURE:
<223> OTHER INFORMATION: Primer
```

<400> SEQUENCE: 16
ccgcattagc acagaagcaa                                               20

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
gcctgctctt actggctgga                                               20

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
tctggctgac tgggaagtgg                                               20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
ccgcaacaac gcaatctatg                                               20

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
gcactgcttc ccgaatgtct                                               20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
accaaagcca gcacatagga                                               20

<210> SEQ ID NO 22
<211> LENGTH: 20
<212> TYPE: DNA
<213> ORGANISM: Artificial
<220> FEATURE:
<223> OTHER INFORMATION: Primer

<400> SEQUENCE: 22
ggggcattaa ctgcatctgg                                               20

-continued

```
<210> SEQ ID NO 23
<211> LENGTH: 22
<212> TYPE: DNA
<213> ORGANISM: Artificial
<220> FEATURE:
<223> OTHER INFORMATION: Primer

<400> SEQUENCE: 23
gcaggtggtt tatgggatgt tt                                              22

<210> SEQ ID NO 24
<211> LENGTH: 22
<212> TYPE: DNA
<213> ORGANISM: Artificial
<220> FEATURE:
<223> OTHER INFORMATION: Primer

<400> SEQUENCE: 24
tttgggttca ggagttgttg tg                                              22

<210> SEQ ID NO 25
<211> LENGTH: 23
<212> TYPE: DNA
<213> ORGANISM: Artificial
<220> FEATURE:
<223> OTHER INFORMATION: Primer

<400> SEQUENCE: 25
cacctgagtt ttgatgttga tgg                                             23

<210> SEQ ID NO 26
<211> LENGTH: 23
<212> TYPE: DNA
<213> ORGANISM: Artificial
<220> FEATURE:
<223> OTHER INFORMATION: Primer

<400> SEQUENCE: 26
tcctgaaagt agccctgtct tgt                                             23

<210> SEQ ID NO 27
<211> LENGTH: 20
<212> TYPE: DNA
<213> ORGANISM: Artificial
<220> FEATURE:
<223> OTHER INFORMATION: Primer

<400> SEQUENCE: 27
aactttggca ttgtggaagg                                                 20

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
ggatgcaggg atgatgttct                                                 20

<210> SEQ ID NO 29
<211> LENGTH: 24
<212> TYPE: DNA
<213> ORGANISM: Artificial
<220> FEATURE:
<223> OTHER INFORMATION: Priemr
```

<400> SEQUENCE: 29
ccaagaacga tagtcaattc caga                                          24

<210> SEQ ID NO 30
<211> LENGTH: 21
<212> TYPE: DNA
<213> ORGANISM: Artificial
<220> FEATURE:
<223> OTHER INFORMATION: Primer

<400> SEQUENCE: 30
catcagtccc aagaaggcaa c                                             21

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
caggatgagg acccaagcac                                               20

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
tcagacagca cgaggcattt                                               20

<210> SEQ ID NO 33
<211> LENGTH: 25
<212> TYPE: DNA
<213> ORGANISM: Artificial
<220> FEATURE:
<223> OTHER INFORMATION: Primer

<400> SEQUENCE: 33
ccctttactc tgaccccttt attgt                                         25

<210> SEQ ID NO 34
<211> LENGTH: 22
<212> TYPE: DNA
<213> ORGANISM: Artificial
<220> FEATURE:
<223> OTHER INFORMATION: Primer

<400> SEQUENCE: 34
tgtcccagca tcttgtgttt ct                                            22

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
tctcccggaa ccgactcttc                                               20

```
<210> SEQ ID NO 36
<211> LENGTH: 21
<212> TYPE: DNA
<213> ORGANISM: Artificial
<220> FEATURE:
<223> OTHER INFORMATION: Primer

<400> SEQUENCE: 36
aactggtccc ctagtgtacg a                                              21

<210> SEQ ID NO 37
<211> LENGTH: 463
<212> TYPE: PRT
<213> ORGANISM: Homo sapience

<400> SEQUENCE: 37
```

| Met | Leu | Leu | Leu | Leu | Pro | Leu | Leu | Trp | Gly | Arg | Glu | Arg | Ala | Glu |
|---|---|---|---|---|---|---|---|---|---|---|---|---|---|---|
| 1 | | | | 5 | | | | | 10 | | | | | 15 |

| Gly | Gln | Thr | Ser | Lys | Leu | Leu | Thr | Met | Gln | Ser | Ser | Val | Thr | Val | Gln |
|---|---|---|---|---|---|---|---|---|---|---|---|---|---|---|---|
| | | | 20 | | | | | 25 | | | | | 30 | | |

Glu Gly Leu Cys Val His Val Pro Cys Ser Phe Ser Tyr Pro Ser His
                35                  40                  45

Gly Trp Ile Tyr Pro Gly Pro Val Val His Gly Tyr Trp Phe Arg Glu
 50                  55                  60

Gly Ala Asn Thr Asp Gln Asp Ala Pro Val Ala Thr Asn Asn Pro Ala
 65                  70                  75                  80

Arg Ala Val Trp Glu Glu Thr Arg Asp Arg Phe His Leu Leu Gly Asp
                 85                  90                  95

Pro His Thr Lys Asn Cys Thr Leu Ser Ile Arg Asp Ala Arg Arg Ser
            100                 105                 110

Asp Ala Gly Arg Tyr Phe Phe Arg Met Glu Lys Gly Ser Ile Lys Trp
        115                 120                 125

Asn Tyr Lys His His Arg Leu Ser Val Asn Val Thr Ala Leu Thr His
130                 135                 140

Arg Pro Asn Ile Leu Ile Pro Gly Thr Leu Glu Ser Gly Cys Pro Gln
145                 150                 155                 160

Asn Leu Thr Cys Ser Val Pro Trp Ala Cys Glu Gln Gly Thr Pro Pro
                165                 170                 175

Met Ile Ser Trp Ile Gly Thr Ser Val Ser Pro Leu Asp Pro Ser Thr
            180                 185                 190

Thr Arg Ser Ser Val Leu Thr Leu Ile Pro Gln Pro Gln Asp His Gly
        195                 200                 205

Thr Ser Leu Thr Cys Gln Val Thr Phe Pro Gly Ala Ser Val Thr Thr
    210                 215                 220

Asn Lys Thr Val His Leu Asn Val Ser Tyr Pro Pro Gln Asn Leu Thr
225                 230                 235                 240

Met Thr Val Phe Gln Gly Asp Gly Thr Val Ser Thr Val Leu Gly Asn
                245                 250                 255

Gly Ser Ser Leu Ser Leu Pro Glu Gly Gln Ser Leu Arg Leu Val Cys
            260                 265                 270

Ala Val Asp Ala Val Asp Ser Asn Pro Pro Ala Arg Leu Ser Leu Ser
        275                 280                 285

Trp Arg Gly Leu Thr Leu Cys Pro Ser Gln Pro Ser Asn Pro Gly Val
    290                 295                 300

Leu Glu Leu Pro Trp Val His Leu Arg Asp Ala Ala Glu Phe Thr Cys
305                 310                 315                 320

-continued

```
Arg Ala Gln Asn Pro Leu Gly Ser Gln Gln Val Tyr Leu Asn Val Ser
            325                 330                 335

Leu Gln Ser Lys Ala Thr Ser Gly Val Thr Gln Gly Val Val Gly Gly
            340                 345                 350

Ala Gly Ala Thr Ala Leu Val Phe Leu Ser Phe Cys Val Ile Phe Val
            355                 360                 365

Val Val Arg Ser Cys Arg Lys Lys Ser Ala Arg Pro Ala Ala Gly Val
        370                 375                 380

Gly Asp Thr Gly Ile Glu Asp Ala Asn Ala Val Arg Gly Ser Ala Ser
385                 390                 395                 400

Gln Gly Pro Leu Thr Glu Pro Trp Ala Glu Asp Ser Pro Pro Asp Gln
            405                 410                 415

Pro Pro Pro Ala Ser Ala Arg Ser Ser Val Gly Glu Gly Glu Leu Gln
            420                 425                 430

Tyr Ala Ser Leu Ser Phe Gln Met Val Lys Pro Trp Asp Ser Arg Gly
            435                 440                 445

Gln Glu Ala Thr Asp Thr Glu Tyr Ser Glu Ile Lys Ile His Arg
        450                 455                 460
```

COMPOSITION HAVING TISSUE-REPAIRING ACTIVITY, AND USE THEREFOR

This is a Continuation of application Ser. No. 15/938,839 filed Mar. 28, 2018 (now U.S. Pat. No. 10,507,230), which is a Division of application Ser. No. 14/654,624 filed Jun. 22, 2015 (now U.S. Pat. No. 9,962,428), which in turn is a U.S. National Phase of International Application No. PCT/JP2013/084523 filed Dec. 24, 2013, which claims the benefit of Japanese Application No. 2012-280022 filed Dec. 21, 2012. The disclosure of the prior applications is hereby incorporated by reference herein in their entirety.

This is a Continuation of application Ser. No. 15/938,839 filed Mar. 28, 2018, which is a Division of application Ser. No. 14/654,624 filed Jun. 22, 2015, which in turn is a U.S. National Phase of International Application No. PCT/JP2013/084523 filed Dec. 24, 2013, which claims the benefit of Japanese Application No. 2012-280022 filed Dec. 21, 2012. The disclosure of the prior applications is hereby incorporated by reference herein in their entirety.

TECHNICAL FIELD

The present Description relates to a composition having tissue-repairing activity in inflammatory disorders, and to a use therefor.

BACKGROUND ART

An inflammatory reaction is a series of processes associated with the elimination of foreign matter and pathogens and the protection and repair of tissue. In the course of an inflammatory reaction, there is also a parallel immune reaction that actively eliminates foreign contaminants at the same time. For example, in tissues other than the central nervous system, macrophages ingest and digest bacteria and viruses or dead cells invading into the living body. They also perform antigen presentation, contributing to antibody production by B-cells. In the central nervous system, the role of the macrophages is played by a type of immunocompetent cell called microglia.

Two types of microglia and macrophages are known: the tissue-destroying type and the tissue-repairing type (Non Patent Literature 1, Non Patent Literature 2). The process of eliminating pathogens and protecting tissue in inflammatory reactions is characterized by the aggregation of tissue-destroying microglia and macrophages. However, if excess aggregation occurs it may cause injury to the body's own tissue and increased pain. In the tissue-repairing process, on the other hand, the tissue-repairing microglia and macrophages promote tissue repair.

A composition containing culture supernatant of dental pulp stem cells or other stem cells has been described as effective for treating injuries (Patent Literature 1).

CITATION LIST

Patent Literature

Patent Literature 1: WO 2011/118795

Non Patent Literature

Non Patent Literature 1: David, S. & Kroner, A., Nature Reviews Neuroscience, 12(7), 388-399

Non Patent Literature 2: Popovich, P. G. & Longbrake, E. E., Nature Reviews Neuroscience, 9(6), 481-493

SUMMARY

In tissue undergoing an inflammatory reaction, actively promoting the occurrence of tissue-repairing microglia and macrophages among the tissue-destroying microglia and macrophages is thought to be effective for treating the inflammations. Tissue-repairing microglia and macrophages also cause an increase in anti-inflammatory cytokines, and increasing these in tissue subject to inflammatory reactions is also believed to be effective.

At present, however, no factor or method has yet been provided for inducing or promoting an increase in tissue-repairing microglia or macrophages. Moreover, no factor or method has been provided for promoting anti-inflammatory cytokines.

The present Description provides a tissue-repair agent capable of promoting a reaction associated with tissue repair in tissue that has been or may be injured, including tissue undergoing an inflammatory reaction, as well as a use therefor. At the same time, these disclosures also provide the following tissue repair agent and a use therefor.

After studying various components contained in the culture supernatant of dental pulp stem cells and other stem cells, the inventors discovered that three specific components induce tissue-repairing microglia/macrophages or cause an increase in anti-inflammatory cytokines in inflamed tissue. The inventors also discovered that at least some of these components are effective for healing when applied to tissue undergoing an inflammatory reaction. The present Description provides the following means based on these findings.

(1) A composition having tissue-repairing activity containing at least one component selected from the group consisting of:
   a first component being a protein having a monocyte chemotactic protein-1 (MCP-1) activity;
   a second component being a protein having the extracellular domain activity of sialic acid-binding immunoglobulin-type lectin-9 (Siglec-9); and
   a third component that is at least one of chondroitin sulfate and chondroitin sulfate proteoglycan.

(2) The composition according to (1) or (2), containing both the first component and the second component.

(3) The composition according to (1) or (2), wherein the first component has an amino acid sequence having 60% or more identity with the amino acid sequence represented by SEQ ID NO:2.

(4) The composition according to any of (1) to (3), wherein the second component has an amino acid sequence having 60% or more identity with the amino acid sequence represented by SEQ ID NO:4.

(5) The composition according to any of (1) to (4), containing chondroitin sulfate or chondroitin sulfate proteoglycan.

(6) The composition according to any of (1) to (5), containing the first component and the second component in an amount effective to produce an activity described in (a) or (b) below:
   (a) an activity of inducing tissue-repairing macrophages and/or microglia in inflamed tissue; or
   (b) an activity of promoting production of anti-inflammatory cytokines.

(7) A composition for an anti-inflammatory agent being the composition according to any of (1) to (6).

(8) The composition according to (7), wherein the composition is for the treatment of a central nervous system disorder selected from the group consisting of spinal cord injury, cerebral infarction, neonatal hypoxic ischemia, Alzheimer's disease, multiple sclerosis, amyotrophic lateral sclerosis and Parkinson's disease.

(9) The composition according to (7), wherein the composition is for the treatment of a non-central nervous system disorder selected from the group consisting of severe hepatitis, acute hepatitis, chronic hepatitis, acute and chronic interstitial pneumonia, type I and type II diabetes, Sjogren's syndrome, dry eye, rheumatoid arthritis, systemic erythematosus, skin injury, myocardial infarction, and immune rejection accompanying bone marrow transplant.

(10) An inducer of tissue-repairing macrophages and/or microglia, containing at least one selected from the group consisting of:
  a first component being a protein having a monocyte chemotactic protein-1 (MCP-1) activity;
  a second component being a protein having the extracellular domain activity of sialic acid-binding immunoglobulin-type lectin-9 (Siglec-9); and
  a third component being at least one of chondroitin sulfate and chondroitin sulfate proteoglycan.

(11) A promoter of anti-inflammatory cytokine production, containing at least one selected from the group consisting of:
  a first component being a protein having a monocyte chemotactic protein-1 (MCP-1) activity;
  a second component being a protein having the extracellular domain activity of sialic acid-binding immunoglobulin-type lectin-9 (Siglec-9); and
  a third component being at least one of chondroitin sulfate and chondroitin sulfate proteoglycan.

(12) A method of producing tissue-repairing microglia or macrophages, comprising a step of culturing microglia or macrophages ex vivo in the presence of at least one selected from the group consisting of:
  a first component being a protein having a monocyte chemotactic protein-1 (MCP-1) activity;
  a second component being a protein having the extracellular domain activity of sialic acid-binding immunoglobulin-type lectin-9 (Siglec-9); and
  a third component that is at least one of chondroitin sulfate and chondroitin sulfate proteoglycan.

(13) A microglia/macrophage reagent kit, containing at least one selected from the group consisting of:
  a first component being a protein having a monocyte chemotactic protein-1 (MCP-1) activity;
  a second component being a protein having the extracellular domain activity of sialic acid-binding immunoglobulin-type lectin-9 (Siglec-9); and
  a third component being at least one of chondroitin sulfate and chondroitin sulfate proteoglycan.

(14) The reagent kit according to (13), containing both the first component and the second component.

(15) A method for promoting tissue repair by delivering, to an injured tissue or inflamed tissue, at least one selected from the group consisting of:
  a first component being a protein having a monocyte chemotactic protein-1 (MCP-1) activity;
  a second component being a protein having the extracellular domain activity of sialic acid-binding immunoglobulin-type lectin-9 (Siglec-9); and
  a third component being at least one of chondroitin sulfate and chondroitin sulfate proteoglycan.

(16) A tissue-repair agent containing at least one component selected from the group consisting of a first component having a monocyte chemotactic protein-1 (MCP-1) activity, a second component having the extracellular domain activity of sialic acid-binding immunoglobulin-type lectin-9 (Siglec-9), and a third component being at least one of chondroitin sulfate and chondroitin sulfate proteoglycan.

(17) The tissue-repair agent according to (16), containing at least one or both of the first component and the second component.

(18) The tissue repair agent according to (16) or (17), containing both the first component and the second component.

(19) The tissue repair agent according to any of (16) to (18), wherein the first component has an amino acid sequence having 60% or more identity with the amino acid sequence represented by SEQ ID NO:2.

(20) The tissue repair agent according to any of (16) to (19), wherein the second component has an amino acid sequence having 60% or more identity with the amino acid sequence represented by SEQ ID NO:4.

(21) The tissue repair agent according to any of (16) to (20), containing the third component.

(22) The tissue repair agent according to any of (16) to (21), containing one or more components selected from the group consisting of the first component, the second component and the third component in an amount effective for producing an activity described in (a) or (b) below:
  (a) an activity of inducing tissue-repairing macrophages and/or microglia in inflamed tissue; or
  (b) an activity of promoting production of anti-inflammatory cytokines.

(22) An anti-inflammatory agent having the tissue-repair agent according to any of (16) to (21) as an active ingredient.

(23) A preventive or treatment agent for a central nervous system disorder selected from the group consisting of spinal cord injury, cerebral infarction, neonatal hypoxic ischemia, Alzheimer's disease, multiple sclerosis, amyotrophic lateral sclerosis and Parkinson's disease, the preventive or treatment agent having the tissue-repair agent according to any of (16) to (21) as an active ingredient.

(24) A preventive or treatment agent for a non-central nervous system disorder selected from the group consisting of severe hepatitis, acute hepatitis, chronic hepatitis, acute and chronic interstitial pneumonia, type I and type II diabetes, Sjogren's syndrome, dry eye, rheumatoid arthritis, systemic erythematosus, skin injury, myocardial infarction, and immune rejection accompanying bone marrow transplant, the preventive or treatment agent having the tissue-repair agent according to any of (16) to (21) as an active ingredient.

(25) An inducer of tissue-repairing macrophages and/or microglia, containing at least one selected from the group consisting of a first component that is a protein having a monocyte chemotactic protein-1 (MCP-1) activity, a second component that is a protein having the extracellular domain activity of sialic acid-binding immunoglobulin-type lectin-9 (Siglec-9), and a third component that is at least one of chondroitin sulfate and chondroitin sulfate proteoglycan.

(26) A promoter of anti-inflammatory cytokine production, containing at least one selected from the group consisting of a first component that is a protein having a monocyte chemotactic protein-1 (MCP-1) activity, a second component that is a protein having the extracellular domain activity of sialic acid-binding immunoglobulin-type lectin-9 (Siglec-9), and a third component that is at least one of chondroitin sulfate and chondroitin sulfate proteoglycan.

(27) A method of producing tissue-repairing microglia or macrophages, provided with a step of culturing microglia or macrophages ex vivo in the presence of at least one selected from the group consisting of a first component that is a protein having a monocyte chemotactic protein-1 (MCP-1) activity, a second component that is a protein having the extracellular domain activity of sialic acid-binding immunoglobulin-type lectin-9 (Siglec-9), and a third component that is at least one of chondroitin sulfate and chondroitin sulfate proteoglycan.

(28) A microglia/macrophage reagent kit, containing at least one selected from the group consisting of a first component that is a protein having a monocyte chemotactic protein-1 (MCP-1) activity, a second component that is a protein having the extracellular domain activity of sialic acid-binding immunoglobulin-type lectin-9 (Siglec-9), and a third component that is at least one of chondroitin sulfate and chondroitin sulfate proteoglycan.

(29) The reagent kit according to (28), containing both the first component and the second component.

(30) A method for promoting tissue repair by delivering, to an injured tissue or inflamed tissue, at least one selected from the group consisting of a first component that is a protein having a monocyte chemotactic protein-1 (MCP-1) activity, a second component that is a protein having the extracellular domain activity of sialic acid-binding immunoglobulin-type lectin-9 (Siglec-9), and a third component that is at least one of chondroitin sulfate and chondroitin sulfate proteoglycan.

BRIEF DESCRIPTION OF DRAWINGS

FIGS. 6A, 6B, 6C, 6D, 6E, and 6F show the synergistic effects of MCP-1, ED-Siglec-9 and CSPG on induction of tissue-repairing microglia;

FIGS. 7A, 7B, and 7C show the synergistic effects of MCP-1, ED-Siglec-9 and CSPG on induction of tissue-repairing microglia, with the upper photograph in FIG. 7A showing the results of GFAP and H-E staining, and the lower part showing quantitative results for tissue loss area 8 weeks after SCI, while FIG. 7B shows an immunohistological image of 5-HT-positive nerve fiber, and FIG. 7C shows quantitative results for 5-HT-positive nerve fiber 5 mm on the caudal side and 5 mm on the rostral side of an epicenter of tissue loss;

FIG. 11A shows results for THP-1 lysate immune precipitated with ED-Siglec-9 and CCR2 and immunoblotted with anti-CCR2 antibody or MAH lectin, FIG. 11B shows that CSPG treatment increases the CCR2 signaling of microglia, and FIG. 11C shows that ED-Siglec-9 interacts physically with CCR2 in microglia;

FIGS. 21A, 21B, and 21C shows long-term arthritis suppression effects from ED-Siglec-9 administration;

FIG. 22A shows that ED-Siglec-9 administration suppresses increased expression of TNF-α caused by LPS stimulus, while

DESCRIPTION OF EMBODIMENTS

Figure 1:
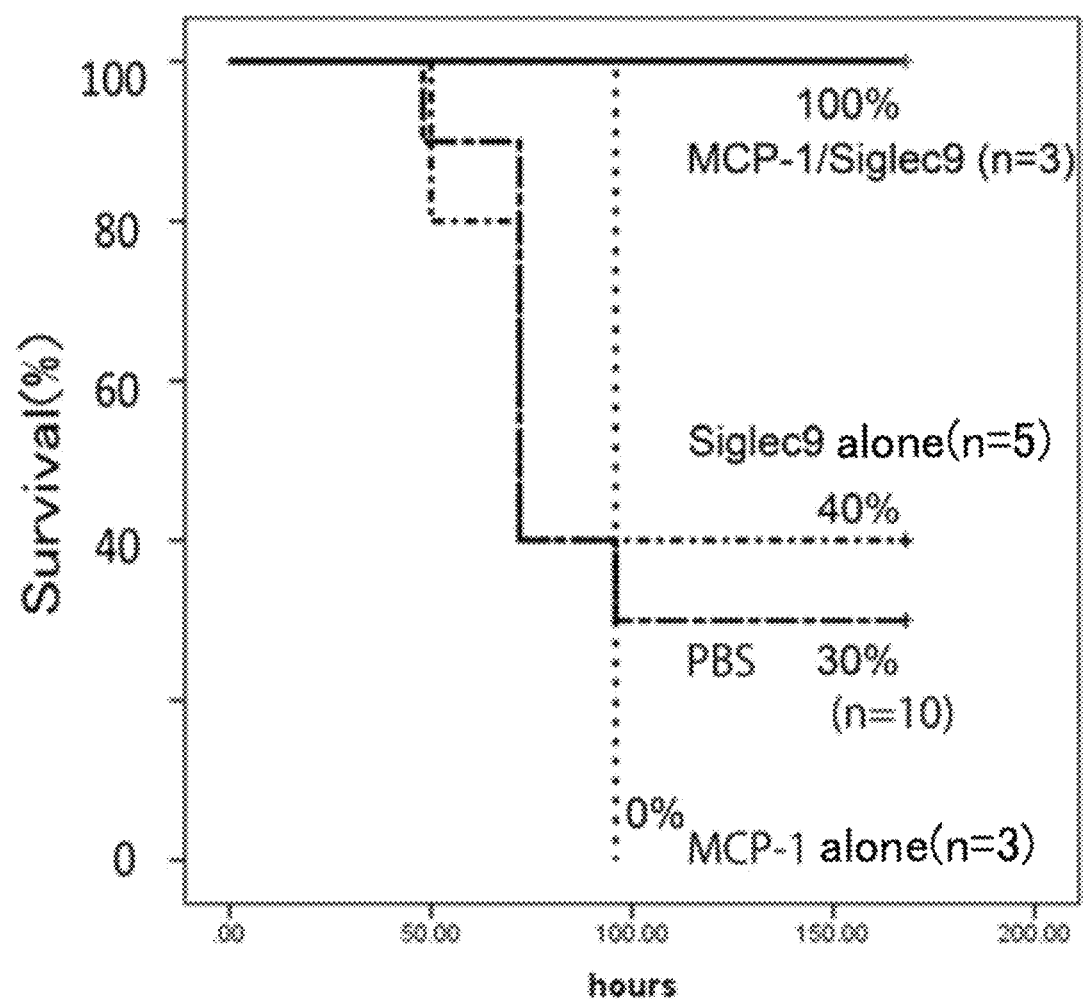
FIG. 1 shows survival rates in severe hepatitis model rats.

The present Description relates to a composition having tissue-repairing activity (tissue repair agent, hereunder simply called "the agent") containing at least one component selected from the group consisting of a first component that is a protein having a monocyte chemotactic protein-1 (MCP-1) activity, a second component that is a protein having the extracellular domain activity of sialic acid-binding immunoglobulin-type lectin-9 (Siglec-9), and a third component that is at least one of chondroitin sulfate and chondroitin sulfate proteoglycan, and to a use therefor. By including at least one of these components in the agent, it is possible to induce the differentiation or conversion of immunocompetent microglia/macrophage cells into tissue-repairing cells through a synergistic effect with a residual component in the site of tissue repair. Thus, by delivering the agent to an inflammatory reaction site, it is possible to actively apply tissue-repairing microglia/macrophages, and activate tissue repair at the inflammatory reaction site.

The first component, second component and third component may be present at an inflammatory reaction site. When any of these is present, the component that is present at the inflammatory reaction site may be excluded from the agent, or the amount of that component may be reduced. It is known that the first component is found at inflammatory reaction sites. The third component is also a component that is widely found at inflammation sites. Of these, the first component is known to be present at inflammatory reaction sites, and particularly at chronic inflammatory reaction sites. The third component is a constituent of cell membranes and intercellular material. When the first component and third component are present at an inflammatory reaction site, the agent may consist primarily of the second component or may contain only the second component.

The agent preferably contains two or more of these components. By including two or more components, it is possible to more effectively promote conversion of microglia/macrophages. It is more desirable to include all three components.

Of the three components, the agent preferably contains the first component and the second component. The third component (chondroitin sulfate or chondroitin sulfate proteoglycan) is ordinarily present at inflammation sites, and induces tissue-repairing microglia/macrophages in cooperation with the first component and second component. Thus, the agent may consist of only the first component and the second component.

Various embodiments of the disclosures of the present Description are explained in detail below. In the present Description, "repair" means that all or part of a function that has been lost due to injury of a target tissue is maintained or expanded in comparison with the same function of the injured part at the time of the injury. This includes not only restoration of function, but also regeneration of functional tissue. Methods of evaluating whether a function has been maintained or restored differ according to the nature of the injury to the injured part. An assay commonly used to evaluate the external appearance of an injured part or the extent of the target function may be used.

In the present Description, "inflammation" means a mechanism in mammals that is induced by the presence of foreign matter or tissue injury due to some cause, and that acts to protect the body. An "inflammatory reaction" is a series of processes that occur in inflammation. The term "inflammatory reaction" may encompass tissue damage induced by inflammation. An "inflammatory disorder" is a disease, disorder or symptoms characterized by inflammation of bodily tissue or the presence of inflammatory elements. These include local inflammatory reactions and systemic inflammatory reactions.

(Composition Having Tissue-Repairing Activity (Tissue Repair Agent))

The first and second components, which are proteins that may be included in the tissue repair agent disclosed in the present Description, may have been collected from the living bodies of animals and the like, or may have been synthesized chemically or by genetic engineering. Preferably the total protein quantity of the first and second components is at least 50%, or preferably at least 60%, or more preferably at least 70%, or still more preferably at least 80%, or yet more preferably at least 90%, or even more preferably at least 95%, or most preferably at least 98%, or ideally at least 99%, or optimally at least 99.5% of the total protein component of the repair agent. If the total protein quantity of the first and second components is within this range as a percentage of the protein quantity of the composition as a whole, the repair agent has greater tissue repair activity.

(First Component)

The first component is a protein having monocyte chemotactic protein-1 (MCP-1) activity. Homologs of this kind of protein are known in humans and various other animals. In the agent, natural MCP-1 derived from such humans or other animals may be collected from a natural raw material, or the protein may be obtained by chemical or genetic engineering methods. For example, human MCP-1 has the amino acid sequence represented by SEQ ID NO:2 (NCBI Accession NO: NP02973.1). Moreover, human MCP-1 is coded for by DNA consisting of the nucleotide sequence represented by SEQ ID NO:1.

It is sufficient that the first component have MCP-1 activity. That is, it may be either known, natural MCP-1, or a protein that has been newly confirmed to have MCP-1 activity in the agent of the invention. It may also be a protein obtained by modification of natural MCP-1, and having MCP-1 activity in the agent. MCP-1 activity in the agent of the invention may be the ability to induce conversion of microglia/macrophages into the tissue-repairing type in cooperation with the second component and chondroitin sulfate or chondroitin sulfate proteoglycan, or the activity of promoting production of anti-inflammatory cytokines. Such activity can be evaluated easily by a person skilled in the art with reference to the examples discussed below.

For example, the ability to induce conversion of microglia/macrophages into the tissue-repairing type can be evaluated by isolating and culturing microglia/macrophages from mice or the like, supplying a candidate first component to these cultured cells in the presence of the established second component and CS or the like (described below) as necessary, and confirming production of proteins or mRNA of CD206 and Arginase-1, which are markers of tissue-repairing microglia/macrophages.

The activity of promoting production of anti-inflammatory cytokines and the activity of inducing conversion of microglia/macrophages into the tissue-repairing type may also be evaluated by isolating and culturing microglia/macrophages from mice or the like, supplying a candidate first component to these cultured cells in the presence of the established second component and CS or the like (described below) as necessary, and confirming production of IL-10, TGF-$\beta$1 and other anti-inflammatory cytokines.

The activity described above is sufficient as the MCP-1 activity of the modified MCP-1 or other first component, regardless of degree. Preferably, it is at least 50%, or more preferably at least 60%, or still more preferably at least 70%, or yet more preferably at least 80%, or most preferably at least 90% or ideally at least 100% of the MCP-1 activity of a protein consisting of the amino acid sequence represented by SEQ ID NO:1.

Apart from known MCP-1, the first component may be a protein having a specific relationship with MCP-1 sequence data published in a database or the like. An example of such an embodiment is a protein consisting of a published amino acid sequence with one or more amino acids deleted, substituted or added therein, and having MCP-1 activity. Mutations to the amino acids of a published amino acid sequence, or in other words deletions, substitutions or additions, may be of one of these three kinds or of a combination of two or more kinds. The total number of such mutations is not particularly limited, but is preferably about 1 to 10. More preferably it is 1 to 5. Amino acid substitutions are preferably conservative substitutions, and specifically substitutions belonging to the following groups: (glycine, alanine), (valine, isoleucine, leucine), (aspartic acid, glutamic acid), (asparagine, glutamine), (serine, threonine), (lysine, arginine), (phenylalanine, tyrosine).

Another embodiment is a protein having an amino acid sequence having at least 60% identity with a published MCP-1 amino acid sequence, and having MCP-1 activity. Preferably the degree of identity is at least 65%, or preferably at least 70%, or more preferably at least 80%, or still more preferably at least 85%, or yet more preferably at least 90%, or even more preferably at least 95%, or most preferably at least 98%, or ideally at least 99%.

Identity or similarity in the present Description is a relationship well known in the technical field between two or more proteins or two or more polynucleotides, and is determined by a comparison of sequences. In the present technology, "identity" means the degree of sequence invariance between proteins or polynucleotides as determined by alignment between protein or polynucleotide sequences, or alignment among a series of such sequences in some cases. Similarity means the degree of correlation between proteins or polynucleotides as determined by alignment between protein or polynucleotide sequences, or by alignment among a series of partial sequences in some cases. More specifically, it is determined by the identity and conservatism (substitutions in specific amino acids or sequences without sacrificing the physiochemical properties of a sequence) of the sequence. Similarity is called "similarity" in the BLAST sequence homology test results below. The method of determining identity and similarity is preferably a method designed to permit the longest possible alignment between the sequences being compared. Methods for determining identity and similarity are provided by publicly available programs. For example, they can be determined using the BLAST (Basic Local Alignment Search Tool) program of Altschul et al (see for example Altschul S F, Gish W, Miller W, Myers E W, Lipman D J., J. Mol. Biol., 215: pp 403-410 (1990); Altschul S F, Madden T L, Schaffer A A, Zhang J, Miller W, Lipman D J., Nucleic Acids Res. 25: pp 3389-3402 (1997)). When using BLAST or other software the conditions are not particularly limited, but it is desirable to use the default values.

In addition to the amino acid sequences and nucleic acid sequences of known MCP-1, various proteins that can be used as the first component include proteins that have a specific relationship with known amino acid or nucleotide sequences of MCP-1, and have MCP-1 activity in the present Description. The chemokine ligand (CCL) family is one example. Typical examples include CCL13, CCL7, CCL8, CCL11 and the like.

Examples of proteins having at least 60% identity with the amino acid sequence represented by SEQ ID NO:2 include the following four proteins for example.

(1) Human C-C motif chemokine 13 precursor (NCBI Accession NO: NP_005399.1, 65% identity and 82% similarity with amino acid sequence represented by SEQ ID NO:2)

(2) Human C-C motif chemokine 7 precursor (NCBI Accession NO: NP_6264.2, 73% identity, 78% similarity)

(3) Human C-C motif chemokine 8 precursor (NCBI Accession NO: NP_005614.2, 69% identity, 84% similarity)

(4) Human eotaxin precursor (NCBI Accession NO: NP_002977.1, 70% identity, 84% similarity)

Yet another embodiment is a protein coded for by DNA that hybridizes under stringent conditions with DNA consisting of a nucleotide sequence complementary to DNA consisting of a nucleotide sequence coding for published MCP-1, and having MCP-1 activity. Stringent conditions are for example conditions under which a so-called specific hybrid is formed, and non-specific hybrids are not formed. For example, they are conditions under which hybridization occurs with a nucleic acid having a high degree of nucleotide sequence identity, or in other words with a complementary strand of DNA consisting of a nucleotide sequence having at least 70% or preferably at least 80% or more preferably at least 85% or still more preferably at least 90% or yet more preferably at least 95% or even more preferably at least 98% or most preferably at least 99% identity with a published nucleotide sequence, but not with a complementary strand of a nucleic acid having a lower degree of homology. More specifically, they are conditions of sodium salt concentration 15 to 750 mM or preferably 50 to 750 mM or more preferably 300 to 750 mM, temperature 25 to 70° C. or preferably 50 to 70° C. or more preferably 55 to 65° C., and formamide concentration 0 to 50% or preferably 20 to 50% or more preferably 35 to 45%. Moreover, under stringent conditions the filter washing conditions after hybridization are normally sodium salt concentration 15 to 600 mM or preferably 50 to 600 mM or more preferably 300 to 600 mM, and temperature 50 to 70° C. or preferably 55 to 70° or more preferably 60 to 65° C. Thus, a further embodiment is a protein coded for by DNA having a nucleotide sequence that has at least 80% or preferably at least 85% or more preferably at least 90% or still more preferably at least 95% or yet more preferably at least 97% or even more preferably at least 98% or most preferably at least 99% identity with a published nucleotide sequence, and having MCP-1 activity.

Such a protein or DNA coding therefor may be obtained for example as nucleic acid fragments by performing PCR amplification using primers designed based on a published nucleotide sequence or the like, using DNA extracted from various animals or nucleic acids derived from various cDNA libraries or genome DNA libraries as templates. It can also be obtained as nucleic acid fragments by performing hybridization with a nucleic acid derived from such a library as a template, using as a probe a DNA fragment that is a part of a gene coding for MCP-1. A gene may also be synthesized as nucleic acid fragments by chemical synthesis methods or various other nucleic acid sequence synthesis methods known in the technical field.

A protein or DNA coding therefor may also be obtained for example by using common mutagenesis methods, site-specific mutagenesis or molecular evolution methods using error-prone PCR or the like to modify DNA coding for the sequence of a published amino acid. Examples of such methods include known methods such as the Kunkel method and Gapped duplex method, and methods based on these, and for example mutations may be introduced with a mutation introduction kit using site-specific mutagenesis (such as Mutant-K (TAKARA) or Mutant-G (TAKARA)), or with a TAKARA LA PCR in vitro Mutagenesis series kit.

(Second Component)

The second component is a protein having the extracellular domain activity of sialic acid-binding immunoglobulin-type lectin-9 (Siglec-9). Homologs of this type of protein and the full-length protein are known in humans and various other animals. Siglec-9 is a transmembrane protein that is expressed in monocytes, granulocytes and macrophages, and has an extracellular domain, a transmembrane domain and a cytoplasm domain. In the present Description, the extracellular domain of Siglec-9 can be used by preference. The extracellular domain is known to contain an immunoglobulin-like domain.

In the agent of the invention, such natural Siglec-9 derived from humans or other animals may be collected from a natural raw material, or the protein may be obtained by chemical or genetic engineering methods. For example, human Siglec-9 has the amino acid sequence represented by SEQ ID NO:4. It is coded for by DNA consisting of the nucleic acid sequence represented by SEQ ID NO:3.

It is sufficient that the second component have Siglec-9 extracellular domain activity. That is, it may be either known, natural Siglec-9, or a protein that has been newly confirmed to function as the extracellular domain of Siglec-9 in the agent. It may be also be natural Siglec-9 that has been modified as described above. In terms of the extracellular domain activity of Siglec-9 in the agent, the protein may have the activity of increasing anti-inflammatory cytokines or the ability to induce conversion of microglia into the tissue-repairing type in cooperation with the first component and chondroitin sulfate or chondroitin sulfate proteoglycan.

Human Siglec-9 consists of the amino acid sequence of 463 amino acids represented by SEQ ID NO:37. Of these, the amino acid sequence from No. 1 to No. 17 is a signal peptide. The second component of these disclosures may have the amino acid sequence from position No. 18 to position No. 348 of this amino acid sequence (SEQ ID NO:4), or may have the full-length amino acid sequence of this amino acid sequence, or the amino acid sequence from position No. 18 to position No. 463.

Such activity can be easily evaluated by a person skilled in the art with reference to the examples below, as described above. The inducing activity or production promoting activity described above is sufficient as the Siglec-9 extracellular domain activity in the extracellular domain of modified Siglec-9, regardless of degree.

For example, the ability to induce conversion of microglia/macrophages into the tissue-repairing type can be evaluated by isolating and culturing microglia/macrophages from mice or the like, supplying a candidate second component to these cultured cells in the presence of the established first component and CS or the like as necessary, and confirming proteins or mRNA of CD206 and Arginase-1, which are markers of tissue-repairing microglia/macrophages.

The activity of promoting production of anti-inflammatory cytokines and the ability to induce conversion of microglia/macrophages into the tissue-repairing type may also be evaluated by isolating and culturing microglia/macrophages from mice or the like, supplying a candidate second component to these cultured cells in the presence of the established first component and CS or the like as necessary, and confirming production of IL-10, TGF-β1 and other anti-inflammatory cytokines for example.

Preferably, this activity is at least 50% or more preferably at least 60% or still more preferably at least 70% or yet more preferably at least 80% or most preferably at least 90% or ideally at least 100% of the Siglec-9 extracellular domain activity of a protein consisting of the amino acid sequence represented by SEQ ID NO:4.

In addition to known amino acid sequences and nucleotide sequence of Siglec-9 extracellular domains, various proteins that can be used as the second component include proteins having a specific relationship with known amino acid and nucleotide sequences of Siglec-9 extracellular domains, and having Siglec-9 extracellular domain activity in the present Description. The Siglec family proteins are one example. Typical examples include Siglec-9, Siglec-7, Siglec-12, Siglec-8, CD33 and the like.

Examples of proteins having at least 60% identity with the amino acid sequence represented by SEQ ID NO: 4 include the following ten proteins for example.

(1) Human sialic acid-binding Ig-like lectin 9 isoform 2 precursor (NCBI Accession NO: NP_055256.1, 100% identity and 100% similarity with amino acid sequence represented by SEQ ID NO:4, nucleotide sequence given by SEQ ID NO:5, amino acid sequence by SEQ ID NO:6)

(2) Human sialic acid-binding Ig-like lectin 9 isoform 1 precursor (NCBI Accession NO: NP_001185487.1, 100% identity and 100% similarity with amino acid sequence represented by SEQ ID NO:4)

(3) Human sialic acid-binding Ig-like lectin 7 isoform 1 precursor (NCBI Accession NO: NP_00055220.1, 81% identity and 85% similarity with amino acid sequence represented by SEQ ID NO:4)

(4) Human sialic acid-binding Ig-like lectin 12 isoform b precursor (NCBI Accession NO: NP_2015856.1, 68% identity and 79% similarity with amino acid sequence represented by SEQ ID NO:4)

(5) Human sialic acid-binding Ig-like lectin 12 isoform a precursor (NCBI Accession NO: NP_443729.1, 68% identity and 79% similarity with amino acid sequence represented by SEQ ID NO:4)

(6) Human sialic acid-binding Ig-like lectin 8 precursor (NCBI Accession NO: NP_055257.2, 70% identity and 78% similarity with amino acid sequence represented by SEQ ID NO:4)

(7) Human myeloid cell surface antigen CD33 isoform 3 precursor (NCBI Accession NO: NP_001171079.1, 63% identity and 74% similarity with amino acid sequence represented by SEQ ID NO:4)

(8) Human myeloid cell surface antigen CD33 isoform 1 precursor (NCBI Accession NO: NP_055257.2, 63% identity and 74% similarity with amino acid sequence represented by SEQ ID NO:4)

(9) Human sialic acid-binding Ig-like lectin 7 isoform 2 precursor (NCBI Accession NO: NP_057627.2, 78% identity and 82% similarity with amino acid sequence represented by SEQ ID NO:4)

(10) Human myeloid cell surface antigen CD33 isoform 2 precursor (NCBI Accession NO: NP_001076087.1, 65% identity and 77% similarity with amino acid sequence represented by SEQ ID NO:4)

(Third Component)

The third component is chondroitin sulfate (CS) or chondroitin sulfate proteoglycan (CSPG). According to the inventors, tissue repair activity at inflammatory reaction sites and other tissue injury sites is obtained when the first component, second component and third component are present together. However, because CS and the like are polysaccharides that are ordinarily present in inflamed tissue, the agent may be effective in tissue even if it does not contain these as active ingredients. Of course, the agent will be more reliable or more widely applicable as a composition if it contains the third component. Furthermore, it is desirable to add CS or the like as the third component when the agent is applied ex vivo to an inflamed site or to microglia/macrophages.

The third component may be one that has been collected from a natural source, or may be one that has been synthesized artificially. The form of binding of the sugar in the chondroitin sulfate is not particularly limited. The chondroitin sulfate may also be a mixture of multiple types.

(Compounding of Active Ingredients in the Agent)

Because the agent contains at least one selected from the first component, second component and third component, it can provide tissue repair activity in the presence of a residual component when delivered to an inflamed tissue. Thus, the agent may have one kind of component selected from the group consisting of the first component, second component and third component as an active ingredient, or may have two components as active ingredients, or may have three components as active ingredients. The active ingredients contained in the agent are determined according to the type of disease, the tissue damage site and its properties, and the administration form of the agent. Preferably the agent contains the first component and/or second component. More preferably, it contains the third component in addition to the first component and/or second component.

When the agent contains the first component and/or second component, the concentrations (contents) of the first component and/or second component are not particularly limited. It is sufficient to include an amount effect for producing the tissue-repair activity of the agent. More specifically, it is sufficient that the first component and/or second component be included in amounts effective for producing an activity described in (a) or (b) below in cooperation with the third component, which is present in the agent or at the tissue repair site. These activities may be verified either in vivo or ex vivo in the presence of the third component as necessary:
  (a) the activity of inducing tissue-repairing macrophages or microglia; or
  (b) the activity of promoting production of anti-inflammatory cytokines.

When the agent contains the first component and second component, the compounded ratio of the first component and second component is set as necessary. For example, the mass ratio of the first component to the second component may be set appropriately within the range of 100:1 to 1:100. Preferably, the ratio of the first component to the second component is 1:10 to 10:1. For example, the ratio of first component to the second component may be 5:1 to 1:5, or 2:1 to 1:2 or the like.

When the agent contains the third component, the concentration thereof is not particularly limited. It is sufficient that it be included in an amount effective for producing the tissue-repairing activity of the agent. When the agent also contains the first component and/or second component, the concentration of the third component or the like relative to that of the first and/or second component is not particularly limited, as long as it is an amount effective for producing the tissue-repairing activity. More specifically, it is sufficient to include an amount effective for producing the activity described in (a) or (b) below in cooperation with the first component and/or second component, which is present in the agent or at the tissue repair site. These activities may be verified either in vivo or ex vivo:
  (a) the activity of inducing tissue-repairing macrophages/microglia; or
  (b) the activity of promoting production of anti-inflammatory cytokines.

For example, the compounded ratio of CS or the like may be set as necessary. For example, the mass ratio of CS or the like relative to the total amount of the first component and second component may be set appropriately in the range of 1000:1 to 1:1000, or preferably 100:1 to 1:100, or more preferably 1:10 to 10:1. For example the ratio of CS or the like to the total of the first component and second component may be 5:1 to 1:5, or 2:1 to 1:2 or the like.

The agent can be manufactured by compounding and mixing one or two or more selected from the first component, second component and third component. That is, it can be manufactured by first obtaining (by extraction from natural material, genetic recombination, chemical synthesis or the like), purifying as necessary and then compounding and mixing the respective components. When there is a raw material that contains these components simultaneously, the components may be extracted selectively by affinity chromatography or the like. The concentrations (purities) and compounded ratios of the first and second components relative to the agent as a whole or the total proteins in the agent may be adjusted appropriately.

Because the agent has tissue-repairing activity, it can be used as a repairing composition for injured tissue, to activate repair of and repair tissue damage from various causes. It can also be used as an anti-inflammatory composition to prevent, treat and alleviate various kinds of inflammation. Classifying disorders that are or may be accompanied by tissue injury into central nervous system disorders and non-central nervous system disorders, the central nervous system disorders are not particularly limited, and may include all pathologies involving loss or degeneration of nerve cells in the central nervous system. Examples include spinal cord injury, cerebral infarction, neonatal hypoxic ischemia, neurodegenerative disease (amyotrophic lateral sclerosis, multiple sclerosis, Alzheimer's disease, Parkinson's disease, progressive supranuclear palsy, Huntington's disease, multisystem atrophy, spinocerebellar degeneration, etc.), viral or autoimmune encephalitis, nerve cell loss and degeneration caused by cerebral infarction accompanying cerebral ischemia or intracerebral bleeding, and retinal disorders involving nerve cell damage. Examples of retinal disorders include traumatic retinal detachment, retinal breaks, retinal concussion, optic canal fracture, diabetic retinopathy, age-related macular degeneration, retinitis pigmentosa, glaucoma, choroideremia, Leber's congenital amaurosis, cone dystrophy, familial drusen, central areolar choroidal dystrophy and autosomal dominant optic atrophy. Of these, the agent can be applied by preference to acute and subacute diseases and conditions. Examples include spinal cord injury and cerebral infarction. Other examples include motor dysfunction and perceptual abnormalities caused by peripheral nerve injury.

The non-central nervous system disorders are not particularly limited, and may include all conditions accompanied by loss or degeneration of cells in tissues outside the central nervous system. Examples include type I and type II diabetes, Sjogren's syndrome, dry eye, skin damage, myocardial infarction, immune rejection accompanying bone marrow transplant, arthritis, rheumatoid arthritis, chronic inflammatory joint disease such as osteoarthritis and bone disease associated with increased bone absorption, ileitis, ulcerative colitis, Barrett's syndrome, Crohn's disease and other inflammatory bowel disorders, asthma, acute and chronic interstitial pneumonia, adult respiratory distress syndrome, chronic obstructive airway disorder and other inflammatory lung diseases, trachoma, onchocerciasis, uveitis, sympathetic ophthalmia, endophthalmitis and other inflammatory eye diseases, gingivitis, periodontitis and other chronic inflammatory periodontal diseases, tuberculosis, Hansen's disease, complications of uremia, glomerular nephritis, nephrosis and other inflammatory kidney diseases, sclerodermatitis, psoriasis, eczema and other inflammatory skin diseases, autoimmune disease, immune complex vasculitis, systemic lupus and erythema, systemic lupus erythematosus (SLE), cardiomyopathy, ischemic heart disease, hypercholesterolemia, atherosclerosis and other inflammatory heart diseases, and preeclampsia, chronic liver failure, acute hepatitis, severe hepatitis, brain, cancer and various other diseases involving serious inflammation. Other examples are systemic inflammations including gram-positive or gram-negative bacterial shock, hemorrhagic or anaphylactic shock, and shock induced by chemotherapy methods that respond to proinflammatory cytokines (for example, proinflammatory cytokine-associated shock). Such shock may be induced for example by chemotherapy drugs used in cancer chemotherapy. Other examples include skin transplant rejection and other transplant rejection responses. Of these, the agent may be applied favorably to acute and subacute diseases and conditions. Examples include acute hepatitis and severe hepatitis. At the same time, it can be applied favorably to hepatic cirrhosis, which is the final form of various liver disorders. Other examples include acute and chronic myelitis syndrome. Examples of this disorder include bisphosphonate drug-associated jaw osteonecrosis and acute and chronic myelitis caused by injury or infection. Other examples include bone deformation or loss caused by periodontitis or injury. The agent promotes formation of new bone when administered in such cases of injury and the like.

Of these, examples include rheumatoid arthritis (RA) and other chronic inflammatory join diseases. Rheumatoid arthritis is an inflammatory autoimmune condition of unknown cause characterized chiefly by chronic multiple synovitis, and protracted synovitis can lead to bone and cartilage damage and permanent loss of function.

In diseases (inflammatory diseases) involving chronic tissue injury, administration of the second component alone is effective in some cases because the living body is capable of providing a continuous supply of MCP-1. Therefore, in some cases administration of the second component by itself may be effective for some conditions involving chronic tissue injury including type II diabetes, chronic hepatitis and hepatic cirrhosis as well as chronic and autoimmune disorders such as those described above. In diseases involving acute tissue injury, on the other hand, it is desirable to administer at least the first component and the second component because the supply of MCP-1 from the living body may not be sufficient.

Another example is interstitial lung disease, including idiopathic pulmonary fibrosis (IPF). Interstitial lung disease is an inflammatory disease involving principally the alveoli and the spaces between the alveoli. The pathology of IPF is characterized by fibrosis of the alveolar walls and changes in alveolar structure (honeycomb lung formation), resulting in diminished lung capacity, lung compliance and diffusing capacity, and diminished quality of life for the patient. The course of the disease is chronic or progressive, and the fatality rate can be as high as 80% when the disease becomes acute.

The agent may contain additional components besides the first, second and third components. As discussed below, moreover, it may be formulated in various ways according to the method of administration.

The agent may contain bioabsorbable materials such as hyaluronic acid, collagen, fibrinogen, platelet plasma and the like. The agent may also contain gelling materials such as hyaluronic acid, collagen, fibrin paste and the like. The agent may contain known pharmaceutically acceptable ingredients. For example, it may contain carriers, excipients, disintegrators, buffers, emulsifiers, suspension agents, soothing agents, stabilizers, preservatives, antiseptic agents, physiological saline and the like. Various known ingredients can be used appropriately as these various additives.

The formulation of the agent is not particularly limited, and various known formulations may be adopted. Examples include pills, powders, grains, granules, fine granules, capsules, injections in the form of solids to be dissolved at the time of use, suppositories and other solid forms; liquid injections (intravenous/intramuscular), infusions, drops and other liquids; and eye drops, sprays, lotions, creams, patches and other topical preparations and the like. It may also assume a form that is supported on an indwelling medical device or the like. The agent may also contain a known pharmaceutically acceptable salt.

When the agent contains two or more components, it may be provided as a formulation (mixture) that already contains these two or more components, or as a combination of individual agents (kit) so that the two or more components may be used as necessary, or as a combination (kit) of an individual agent with a mixture of two or more components. These may also be contained in a single container that allows them to be mixed at the time of use.

The dosage form of the agent is not particularly limited, and various known dosage forms may be adopted according to the target site and the disease to be treated. For example, non-oral administration may be either systemic administration or local administration. Specific examples include infusion, embrocation and spraying of the inflammation site. Other examples include intravenous administration, intra-arterial administration, portal vein administration, intradermal administration, subcutaneous administration, intramuscular administration, intraperitoneal administration, intranasal administration, intraoral administration and the like. When the inflamed site is the brain, intranasal administration is preferred.

It is sufficient that the agent be administered in such a way that the first component, second component and third component are present together at the site requiring tissue repair. Thus, the specific dosage form is not particularly limited. For example, the active ingredients administered as a formulation may be administered simultaneously, or they may be administered successively (any types of active ingredients in any order).

The dosage and administration of the agent are not particularly limited, and can be set according to the age, body weight, condition and the like of the test subject.

Test subjects to which the agent may be applied include humans and other mammals (pets, livestock, experimental animals, etc.). Examples include dogs, cats, rabbits, mice, cows, pigs, goats, sheep, horses, monkeys, guinea pigs, rats and mice.

(Inducer of Tissue-Repairing Macrophages and/or Microglia)

The inducer of tissue-repairing macrophages and/or microglia disclosed in this Description contains one or more selected from the group consisting of the first component, the second component and the third component. This inducer is based on the tissue-repairing microglia/macrophage-inducing activity produced by the first component, second component and third component. The first component, second component and third component are as explained previously, and this inducer may be composed or manufactured in various forms in the same way as the agent described above.

(Promoter of Anti-Inflammatory Cytokine Production)

The promoter of anti-inflammatory cytokine production disclosed in this Description contains one or more selected from the group consisting of the first component, the second component and the third component. This production promoter is based on the anti-inflammatory cytokine production promoting action produced by the first component, second component and third component. As in the case of the inducer, the various embodiments of the agent may be applied to this production promoter.

(Method of Producing Tissue-Repairing Microglia or Macrophages)

The method of producing tissue-repairing microglia or macrophages disclosed in this Description may comprise a step of culturing microglia or macrophages ex vivo in the presence of the first component, second component and third component. With this production method, it is possible to manufacture tissue-repairing microglia or macrophages ex vivo. By for example collecting microglia/macrophages from humans or other mammals, inducing (converting) them into tissue-repairing types ex vivo, and then returning them to the original mammals, it is possible to use such tissue-repairing types to activate tissue repair, suppress inflammation reactions and prevent, alleviate or treat inflammation. The inducer may be used in the various forms described above for producing microglia/macrophages in this way.

(Reagent Kit)

The reagent kit disclosed in this Description may be provided with one or more selected from the group consisting of the first component, second component and third component. When it contains two or more components, they may be mixed together in advance, or provided separately for mixing at the time of use. They may be either solid, or liquid, or to be dissolved at the time of use. A dissolving liquid may also be provided separately as necessary. Chondroitin sulfate proteoglycan may also be mixed in advance with the first component and second component, or may be provided separately.

(Method for Promoting Tissue Repair)

The method for promoting tissue repair disclosed in this Description may comprise a step of delivering at least one selected from the group consisting of the first component, the second component and the third component to an inflamed tissue or injured tissue. With this method, it is possible to effectively promote tissue repair or prevent or alleviate tissue damage in the presence of the first through third components in inflamed tissue or injured tissue. This promotion method may also be implemented as a prevention, treatment or alleviation method in cases of inflammatory disease. The various embodiments of the agent explained above may be applied to the first component, second component and third component, and the various embodiments explained with respect to the agent may also be applied to the applicable dosage form (delivery form).

EXAMPLES

The present invention is explained in detail below with examples, but the following examples do not restrict the present invention. In the examples below, percentage are all mass percentages. In the figures mentioned in the examples below, ED-Siglec-9 may be represented as ED-Siglec-9, or simply as Siglec-9 or Siglec.

Example 1

Analysis of Therapeutic Usefulness of Dental Pulp Stem Cells Using Severe Hepatitis Model (1) Preparation of Severe Hepatitis Model Rats A D-galactosamine solution for inducing severe liver damage was prepared by dissolving it in PBS/NaOH solution. This solution was administered intraperitoneally to Sprague-Dawley rats (200 to 250 g) to 1.2 g of D-galactosamine per kg of rat weight). 24 hours after administration blood was taken, and AST and ALT were measured to confirm induction of severe liver damage (severe hepatitis).

(2) Drug Preparation

A 1 µg/ml pBS solution of ED-Siglec-9 (recombinant human Siglec-9 Fc chimera, R & D Systems, chimera protein containing Gln18 to Gly348 of human Siglec-9) alone, a 1 µg/ml PBS solution of MCP-1 recombinant protein (recombinant human MCP-1/CCL2 (Peprotech)) alone and a PBS solution containing 1 µg/ml each of ED-Siglec-9 and MCP-1 recombinant protein were prepared.

(3) Administration 1 ml of each of the three drug solutions prepared in (2) was administered intravenously through the jugular veins of rats 24 hours after onset of severe hepatitis (48 hours after D-galactosamine administration). As a control, 1 ml of PBS was also administered intravenously through the jugular veins of rats 24 hours after onset of severe hepatitis.

Figure 2:
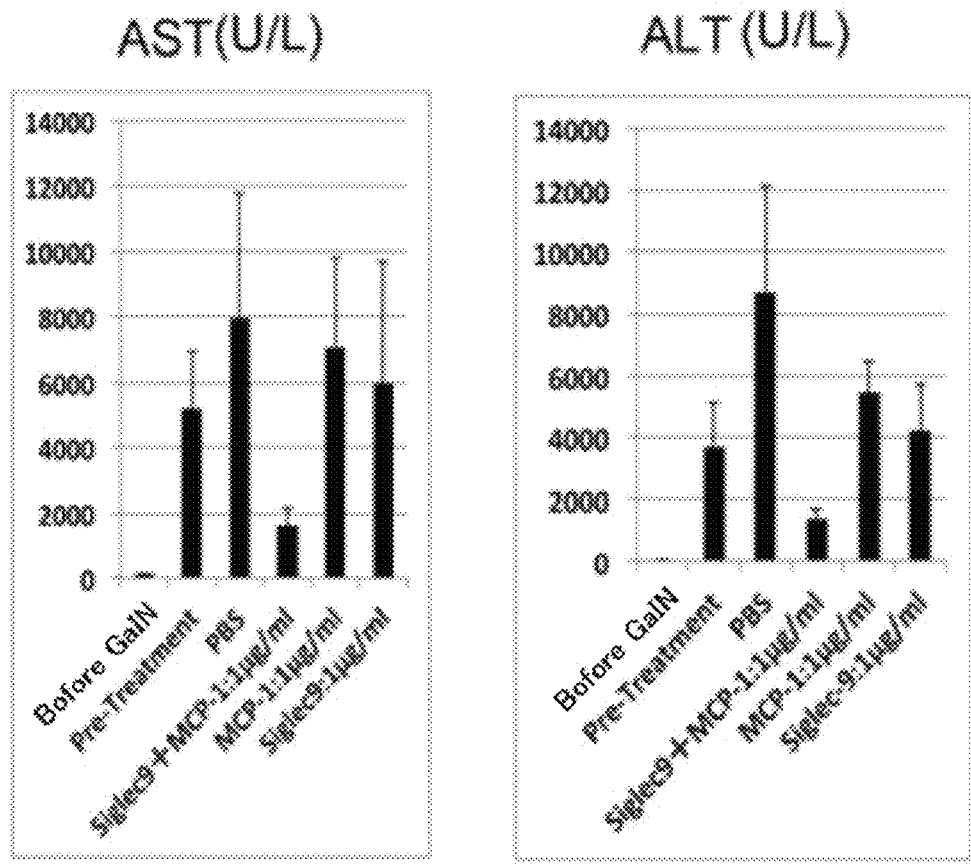
FIG. 2 shows the results of an evaluation of liver damage by blood testing in severe hepatitis model rats.

(4) Determination of 1-Week Survival Rates and Evaluation of Liver Damage by Blood Testing FIGS. 1 and 2 show 1-week survival rates and liver damage as evaluated by blood testing, respectively. A D-galactosamine solution for inducing severe liver damage was administered intraperitoneally at a dosage of 1.2 g/kg to Sprague-Dawley rats (200 to 250 g). As shown in FIG. 1, the 1-week survival rate fell to 30% or less in the PBS administration group. By contrast, the group receiving intravenous administration of the ED-Siglec-9/MCP-1 mixture saw a dramatic clinical improvement, and had a 1-week survival rate of 100%. No clinical improvement was seen in the ED-Siglec-9 and MCP-1 single administration groups. The survival rate was 40% in the ED-Siglec-9 single administration group and 0% in the MCP-1 single administration group.

Moreover, as shown in FIG. 2, while blood AST and ALT were 8000 U/L and 8300 U/L, respectively, in the control group, they were both 2000 U/L or less in the mixed administration group, 6000/4000 U/L in the ED-Siglec-9 single administration group and 7000/5500 U/L in the MCP-1 single administration group. These results are consistent with the survival rates seen in FIG. 1. The benchmark for cell damage was set at AST=6000 U/L, ALT=4000 U/L.

(5) Pathological Analysis of Severe Hepatitis Model

Widespread hepatic cell death and impaired hepatic cell regeneration are generally seen in the livers of severe hepatitis patients. The pathology of the model rats in this case was evaluated by analyzing these factors. Hepatic cell death was evaluated by HE staining and TUNEL staining. The results are shown in FIG. 3.

Figure 3A:
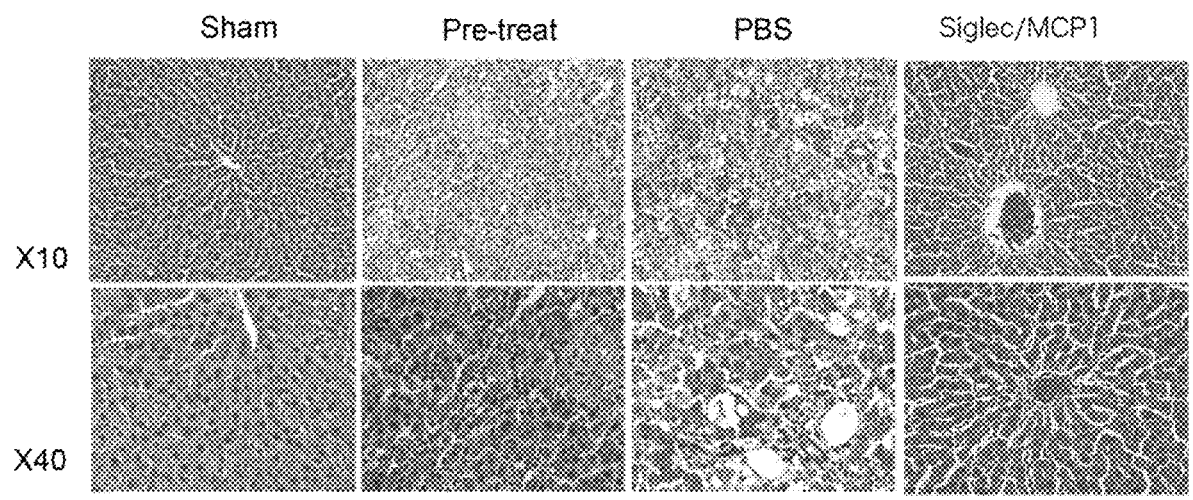
FIGS. 3A and 3B show the results of an evaluation of liver cell death (HE stain and TUNEL stain) in severe hepatitis model rats.
Figure 3B:
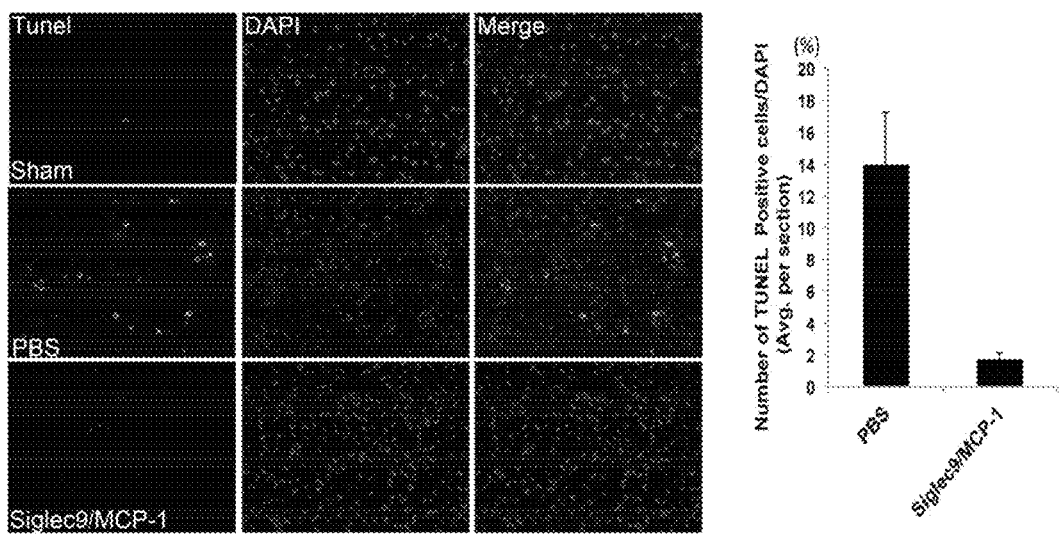

As shown in A and B of FIG. 3, severe vacuolar degeneration and many Tunel-positive cells (20% of total hepatic cells) were detected in the control group. By contrast, the tissue images taken 12 hours after mixed ED-Siglec-9/MCP-1 administration group appeared similar to normal hepatic tissue.

(6) Genetic Analysis of Severe Hepatitis Model

Figure 4:
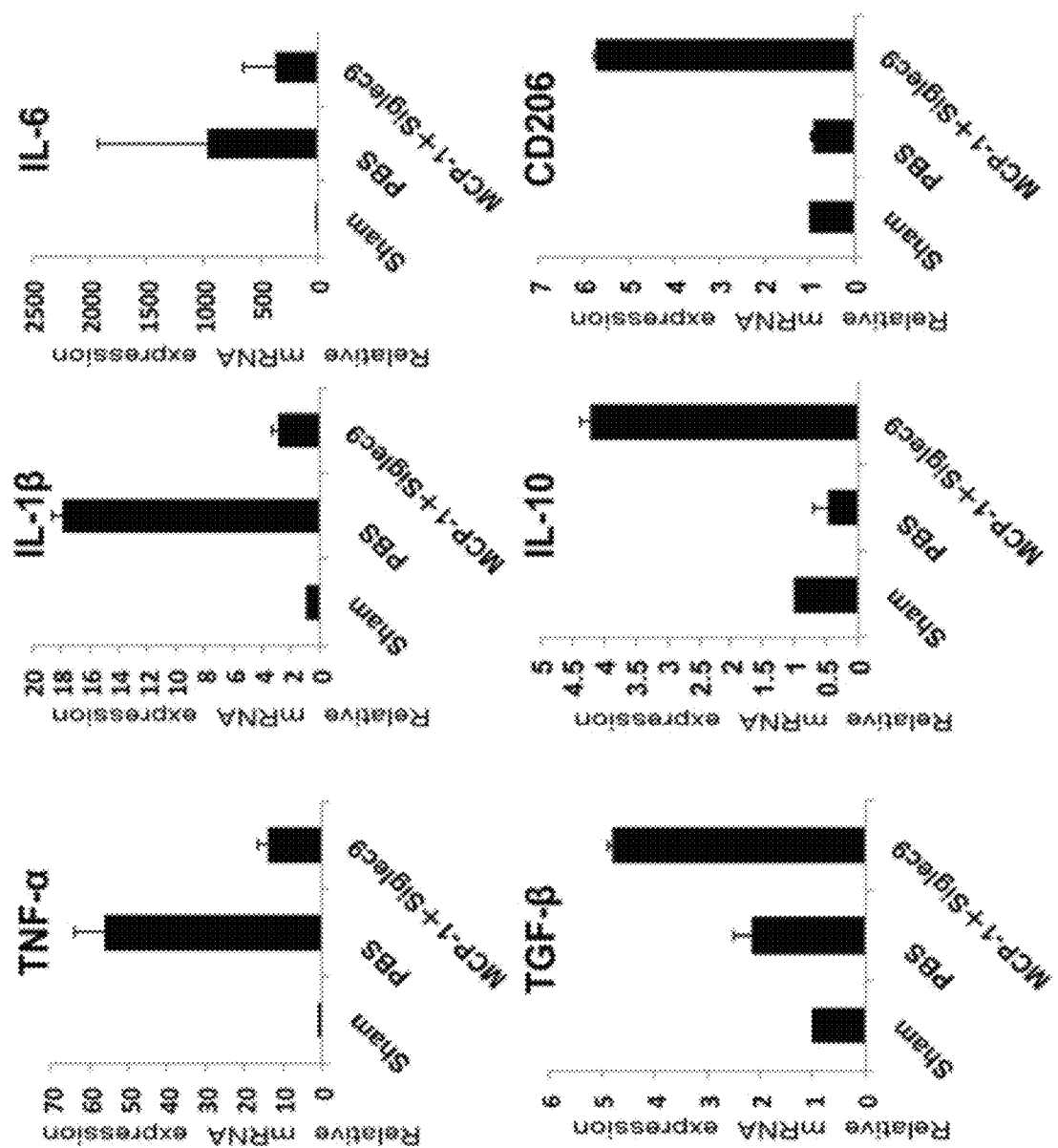
FIG. 4 shows analysis results for gene expression of inflammatory cytokines (TNF-α, IL-1β, IL-6), a dead cell sensor called mannose receptor CD206, and anti-inflammatory cytokines (IL-10, TGF-b) in severe hepatitis model rats.

In severe inflammatory reactions, inflammatory tissue-destroying M1 macrophages and anti-inflammatory tissue-repairing M2 macrophages play an important role in hepatic tissue injury. M1 macrophages promote genetic expression of proinflammatory cytokines (TNF-α, IL-1β, IL-6). M2 macrophages express large quantities of dead cell sensors: mannose receptor CD206 and anti-inflammatory cytokines (IL-10, TGF-b). In the model rats in this case, the produced amounts of these factors were analyzed by quantitative RT-PCR to evaluate pathology. The results are shown in FIG. 4. The primers used in quantitative RT-PCR are shown in Table 1.

As shown in FIG. 4, increased expression of various inflammatory cytokines was seen in the control group. In the ED-Siglec-9/MCP-1 mixed administration group, on the other hand, expression of inflammatory cytokines was suppressed, and expression of anti-inflammatory cytokines was encouraged.

(7) CD206 Immune Staining Results in Severe Hepatitis Model

Figure 5:
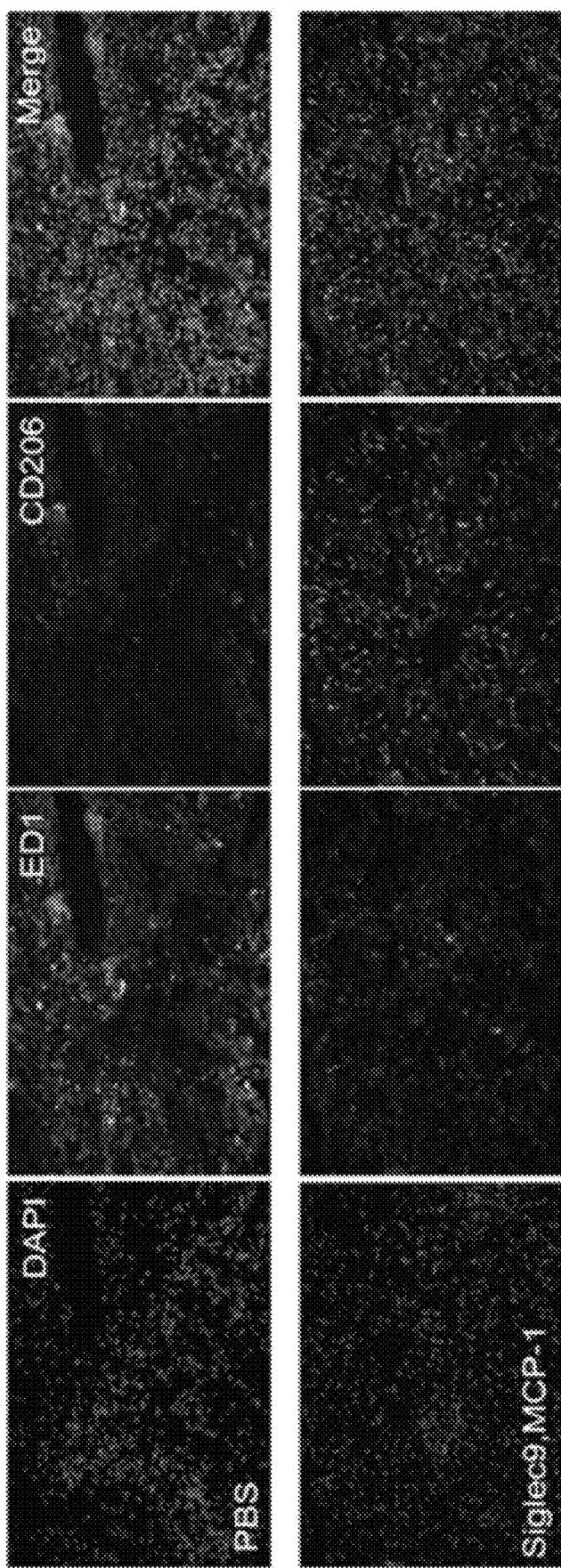
FIG. 5 shows macrophage staining results in severe hepatitis model rats.

FIG. 5 shows the results of CD206 staining in tissues of a severe hepatitis model in the ED-Siglec-9/MCP-1 mixed administration group and control group. As shown in FIG. 5, expression of CD206 was conspicuous in the ED-Siglec-9/MCP-1 mixed administration group, clearly showing conversion into tissue-repairing macrophages.

Example 2

In this example, the effects of MCP-1, ED-Siglec-9 and CSPG were confirmed using mouse microglia and rats with spinal cord injury. The experimental methods are given below, followed by the results.

(1) Isolation and Cell Culture of Mouse Microglia

Primary neurons were isolated from newborn C57BL/6 mice. After 14 days of culture, the microglia were isolated from the cell mixture by the "shaking off" method. The purity of the cultured cells as determined by immune staining of the Fc receptors was 97 to 100%. The culture was maintained in DMEM with 10% fetal bovine serum, 5 µg/ml bovine insulin and 0.2% glucose added thereto.

(2) Microglia CSPG Activation Assay

A 48-well tissue culture plate was coated with 1 µg/ml of poly-L-lysine (PLL; Sigma) or 100 ng/ml of extracellular chondroitin sulfate proteoglycan (CSPG; Millipore). The microglia were seeded $2.0 \times 10^5$ cells/well in serum-free DMEM on the PLL or PLL/CSPG. The serum-free DMEM contained recombinant human MCP-1/CCL2 (Peprotech) and recombinant human ED-Siglec-9 (R & D Systems).

After 24 hours of culture, expression of the CD206 protein and mRNA was analyzed by immunohistological analysis and real-time quantitative PCR, respectively. After 48 hours of culture, the IL-10 concentration of the culture supernatant was measured with an ELISA kit (Quantikine ELISA Mouse IL-10, R & D Systems).

(3) Real-time Q-PCR

Total RNA was quantified with a spectrophotometer, and the condition of the RNA was verified with 1% agarose gel. An RT reaction was performed using Superscript III reverse transcriptase (Invitrogen), using 0.5 µg of total RNA in a total reaction volume of 25 µl. Real-time Q-PCR was performed with a StepOnePlus real-time PCR System (Applied Biosystems) using a THUNDERBIRD SYBR quantitative PCR mix (Toyobo). The primers for the rats and mice were as follows.

TABLE 1

| Origin | Primer | Sequence (forward 5'-3') | SEQ. ID | Sequence (reverse 5'-3') | SEQ. ID |
|---|---|---|---|---|---|
| rat | GAPDH | AACTTTGGCATCGTGGAAGG | 7 | CGGATACATTGGGGGTAGGA | 8 |
| rat | IL-6 | TTGCCTTCTTGGGACTGATG | 9 | ACTGGTCTGTTGTGGGTGGT | 10 |
| rat | IL-1β | CAGGATGAGGACCCAAGCAC | 11 | TCAGACAGCACGAGGCATTT | 12 |
| rat | TNF-α | CTCGAGTGACAAGCCCGTAG | 13 | CCTTGAAGAGAACCTGGGAGTAG | 14 |
| rat | iNOS | GGCAGGATGAGAAGCTGAGG | 15 | CCGCATTAGCACAGAAGCAA | 16 |
| rat | IL-10 | GCCTGCTCTTACTGGCTGGA | 17 | TCTGGCTGACTGGGAAGTGG | 18 |
| rat | TGF-β1 | CCGCAACAACGCAATCTATG | 19 | GCACTGCTTCCCGAATGTCT | 20 |
| rat | VEGF | ACCAAAGCCAGCACATAGGA | 21 | GGGGCATTAACTGCATCTGG | 22 |
| rat | CD206 | GCAGGTGGTTTATGGGATGTTT | 23 | TTTGGGTTCAGGAGTTGTTGTG | 24 |
| rat | Arginase 1 | CACCTGAGTTTTGATGTTGATGG | 25 | TCCTGAAAGTAGCCCTGTCTTGT | 26 |
| mouse | GAPDH | AACTTTGGCATTGTGGAAGG | 27 | GGATGCAGGGATGATGTTCT | 28 |
| mouse | IL-6 | CCAAGAACGATAGTCAATTCCAGA | 29 | CATCAGTCCCAAGAAGGCAAC | 30 |
| mouse | IL-1β | CAGGATGAGGACCCAAGCAC | 31 | TCAGACAGCACGAGGCATTT | 32 |
| mouse | TNF-α | CCCTTTACTCTGACCCCTTTATTGT | 33 | TGTCCCAGCATCTTGTGTTTCT | 34 |
| mouse | CD206 | TCTCCCGGAACCGACTCTTC | 35 | AACTGGTCCCCTAGTGTACGA | 36 |

(4) Rat Contusion Model and Surgical Treatment

Adult female Sprague-Dawley rats weighing 200 to 230 grams were used. The rats were anesthetized by intraperitoneal administration of ketamine (60 to 90 mg/kg) and xylazine (100 to 150 mg/kg). Following Th9 lumbar laminectomy, the dura mater was exposed, and 200 kdyn of traumatic force was applied with a commercial spinal cord injury device (Infinite Horizon Impactor, Precision Systems & Instrumentation). Immediately following spinal cord contusion, a Th12 partial laminectomy was performed, and a thin silicon tube connected to an SMP-200 model iPRECIO (Primetech) was inserted intrathecally under a surgical microscope. The tube was fixed by tying it to a spinous process, and the pump was placed under the skin of the animal's axilla. After surgery, the bladder was compressed and emptied twice a day by manual abdominal pressure. Those animals that exhibited complete paralysis (BBB score=0) on the day after surgery were used in the evaluation. Animals that died immediately or were able to move their hind limbs were excluded from the evaluation.

(5) BBB Open Field Locomotion Score

A hind limb neurobehavioral test was performed using a BBB motor assessment scale. The 22-point (0 to 21) BBB scale is used to evaluate hind leg motor recovery, including joint movement, stepping ability, coordination and trunk stability. A score of 21 signifies the unimpaired movement of an uninjured rat. The animal treatment data were evaluated by two researchers under blind test conditions. The duration of each session was 4 minutes per rat. A repeat measurement variance analysis was performed on the score at each time point using the Tukey multiple comparison test.

(6) Immunohistological Analysis

For histological examination of the treated spinal cords, the animals were anesthetized, and perfused transcardially with a 0.1 MPBS solution of 4% PFA 72 hours and 8 weeks after contusion. The spinal cords were embedded in OCT compound (Sakura Finetek), and cut into 20 μm sagittal or horizontal plane sections in a compartmentalized cryostat (Leica). The tissue sections and microglia were treated by being dipped for 5 minutes in 0.1% (v/v) Triton X-100 PBS solution. After being blocked for 30 minutes with 10% goat serum (v/v), these were incubated with primary antibodies: 5-HT (rabbit IgG, 1:500, Sigma-Aldrich), GFAP (mouse IgG, 1:500, Millipore), Ibal (goat IgG, 1:500, Abcam), CD206 (rabbit IgG, 1:1000, Abcam), IL-10 (mouse IgG, 1:250, Abcam). The secondary antibodies were anti-mouse IgG-Alexa Fluor 488, anti-goat IgG-Alexa Fluor 546 and anti-rabbit IgG-Alexa Fluor 647. Following contrast staining with DAPI (Sigma-Aldrich), the tissue images were observed with a universal fluorescent microscope (BZ9000, Keyence).

(7) Immune Precipitation, Lectin Blot and Western Blot

A lysate of THP-1 cells was immune precipitated using an antibody to ED-Siglec-9 or CCR-2, and the precipitate was immune blotted with an anti-CCR2 antibody or MAH-lectin. For the lectin blot, CCR2 protein that had been immune precipitated with an anti-CCR2 antibody (rabbit IgG, 1:50, Abcam) from a THP-1 (Riken Cell Bank, Japan) lysate (solution buffer: 1% Triton X, 150 mM NaCl, 20 mM tris-HCl, 2 mM calcium chloride) was isolated by SDS-PAGE, and electro-blotted on an Immobilon-P PVDF membrane. After blotting, the membrane was blocked at 4° C. for 12 hours with MAL buffer (10 mM HEPES, pH 7.5, 150 mM NaCl, 0.2% BSA, 0.2% Tween-20). Next, the MAL buffer was probed with 5 mg/ml of biotinylated MAL (Vector Laboratories) at 4° C. for 12 hours. The MAL was detected using avidin-HRP (Vector Laboratories) and ECL (GE Healthcare), and analyzed with a LAS-4000 mini lumino-image analyzer (GE Healthcare).

To analyze the physical interaction between ED-Siglec-9 and CCR2, THP-1 or a native mouse microglia lysate was incubated overnight at 4° C. using 0.15 nM ED-Siglec-9-Fc or Fc, and then immune precipitated with protein A cepharose (GE Healthcare). The total cell lysate or re-suspended precipitate was immunoblotted using an antibody (rabbit IgG, 1:500, Abcam) to mouse CCR2.

(8) Statistics

A repeat measurement variance analysis was performed using the Tukey post-hoc test (SPSS 19.0). A P-value below 0.05 was considered significant.

(Results)

(Synergistic Effects of MCP-1, ED-Siglec-9 and CSPG on Induction of Tissue-Repairing Microglia)

The results for mouse microglia are shown in FIG. 6. As shown in FIGS. 6a to 6d, microglia treated with MCP-1 (50 ng/ml) and ED-Siglec-9 (50 ng/ml) on CSPG exhibited significantly elevated expression of CD-206 at the protein level and at the gene level, as well as increased IL-10 production. In the microglia treated with MCP-1 (50 ng/ml) and ED-Siglec-9 (50 ng/ml) on CSPG, expression of tissue-repairing microglia was also confirmed by immune staining for CD206. As shown in FIGS. 6e and 6f, moreover, the increases in the tissue-repairing microglia marker CD206 and the anti-inflammatory cytokine IL-10 were dependent on the MCP-1/ED-Siglec-9/CSPG concentration.

Figure 7C:
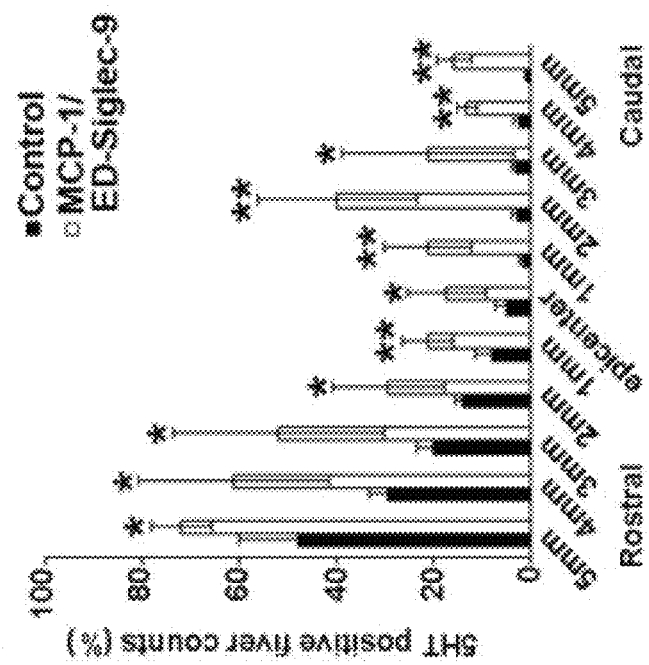
Figure 7B:
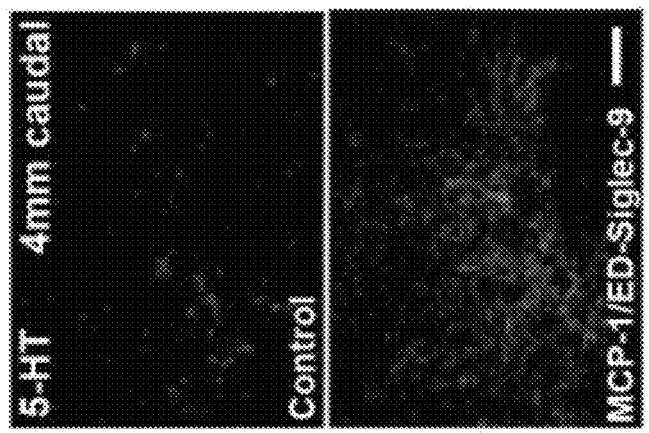
Figure 7A:
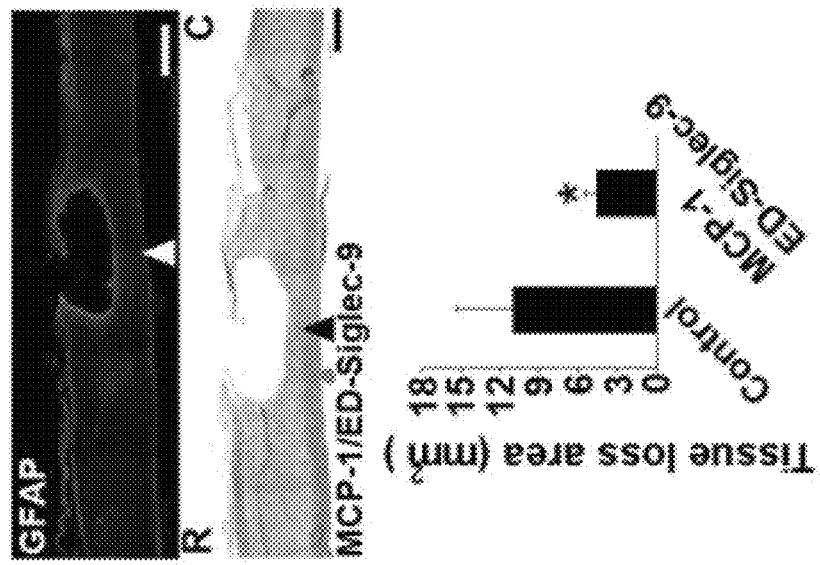

In the treated sections, as shown in FIG. 7a, the GAFP and H-E stains show that 8 weeks after SCI, there was a reduction in both the activity of GFAP-positive astrocytes and the area of tissue injury. Moreover, as shown in FIG. 7b, the results for 5-HT show that repair of positive nerve fibers had progressed 8 weeks after SCI. Furthermore, as shown in FIG. 7c, the 5-HT stain also showed progress in the repair of nerve fibers extending towards the head and tail from the center of the injury.

(Conversion of Inflammatory Spinal Cord Injury to Anti-Inflammatory State and Tissue-Repair State Due to Intrathecal Administration of MCP-1 and ED-siglec-9)

Figure 8:
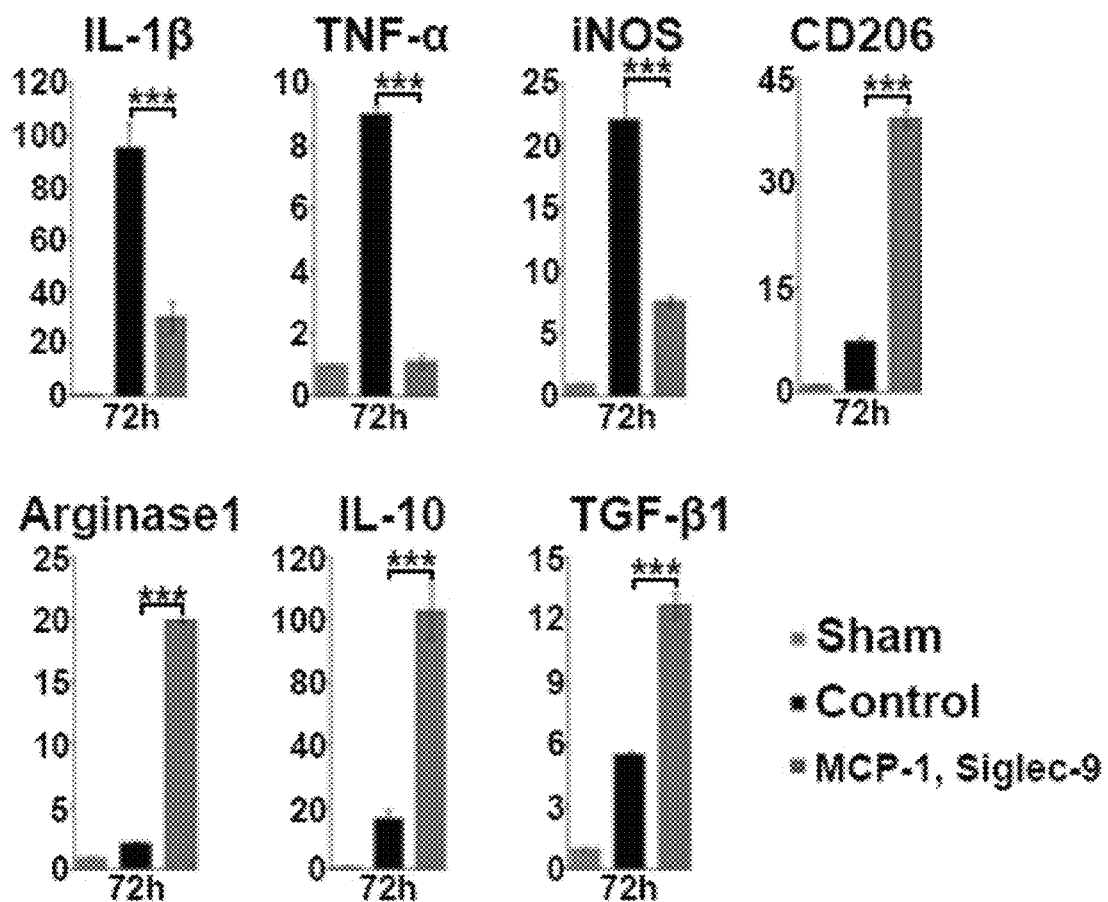
FIG. 8 shows results for gene expression of cytokines and cell surface markers in spinal cord injury sites, as evaluated by quantitative RT-PCR.

3 μl/h each of MCP-1 and ED-Siglec-9 at concentrations of 1 μg/ml were delivered via an iPRECIO injection pump to the SCI site. A silicon tube was inserted into the subarachnoid space. Genetic expression of cytokines and cell surface markers in the spinal cord injury site was evaluated by quantitative RT-PCR analysis. Total RNA was collected from the lesion site 72 hours after SCI. The results are shown in FIG. 8. The Y-axis shows percentages relative to the values for a sham surgery model.

As shown in FIG. 8, inflammatory cytokines (IL-1β, TNF-α) and induced nitric oxide synthesis (iNOS) were increased in the control but dramatically suppressed by combined administration of MCP-1 and ED-Siglec-9. MCP-1 and ED-Siglec-9 administration caused an increase in anti-inflammatory cytokine expression (IL-10 and TGF-β1) and M2 microglia/macrophage markers (CD206, Arginase-1). The experiment was performed three times, and similar results were obtained all three times. The data in FIG. 8 show average±SEM (*P<0.05, P<0.01, *P<0.001).

(Promoting Differentiation of Microglia/Macrophages into Tissue-Repairing Type with MCP-1/ED-Siglec-9 After Spinal Cord Injury)

Figure 9:
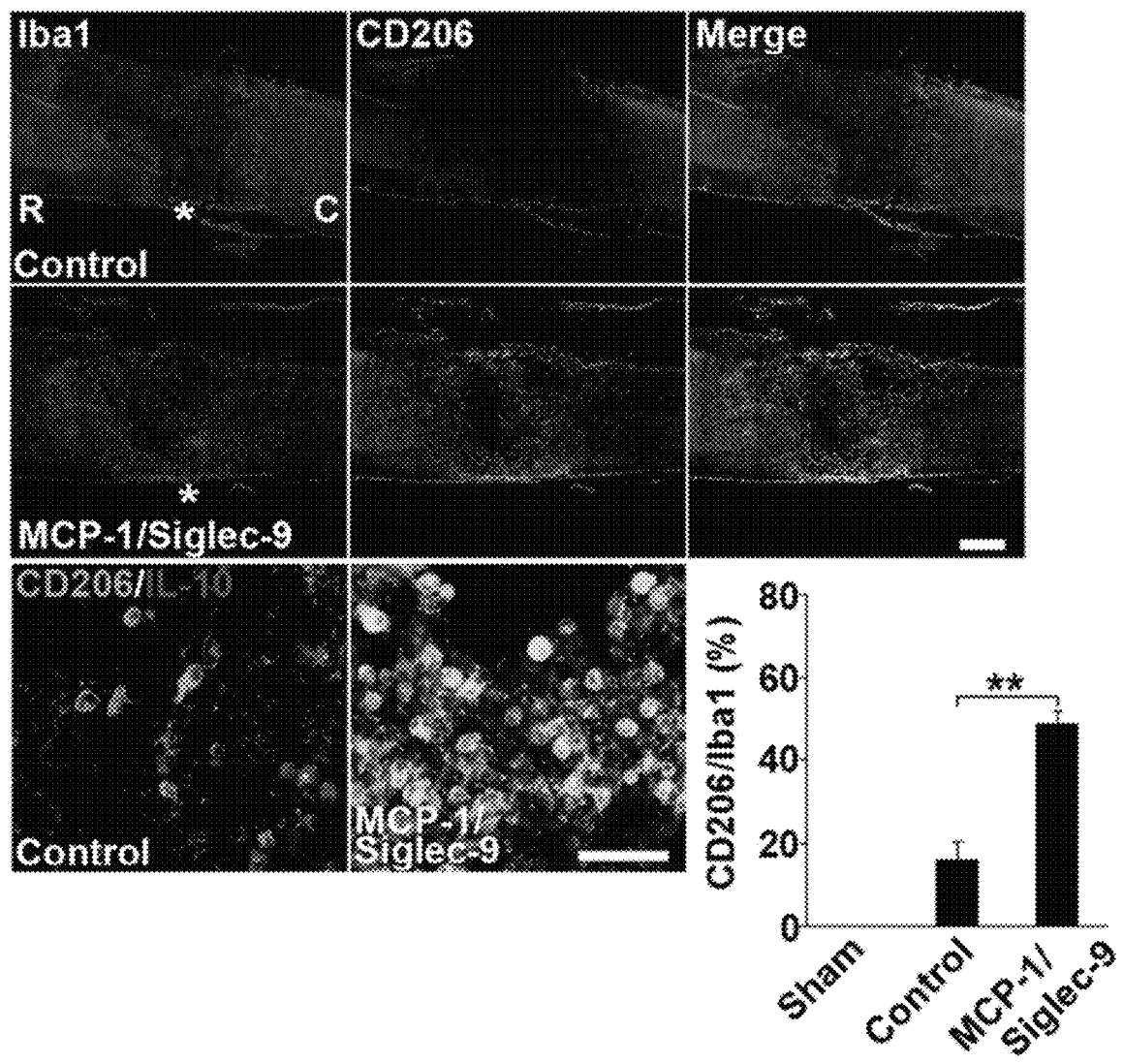
FIG. 9 shows typical images and quantitative results for microglia/macrophages surrounding sites 72 hours after spinal cord injury.

FIG. 9 shows typical images and quantitative results for microglia/macrophages surrounding injury sites 72 hours after spinal cord injury. As shown in the top of FIG. 9, Ibal+ microglia were observed in the control group, but no CD206+ cells were observed. By contrast, as shown in the middle of FIG. 9, 72 hours after spinal cord injury multiple Iba+ cells had migrated to the injury site in the MCP-1/ED-Siglec-9 treated rats, and most of these Ibal+ cells also co-expressed CD206. As shown at the bottom of FIG. 9, moreover, the CD206+ cells in the injury sites of the control rats were not observed to simultaneous express of IL-10, while the CD206+ cells at the injury sites treated with MCP-1/ED-Siglec-9 simultaneously expressed IL-10. The data in the figure show average±SD (*P<0.05, **P<0.01, MCP-1/ED-Siglec-9 treated spinal cord injury model in comparison with PBS treatment).

(Therapeutic Benefits of MCP-1/ED-Siglec-9 for Spinal Cord Injury)

Figure 10:
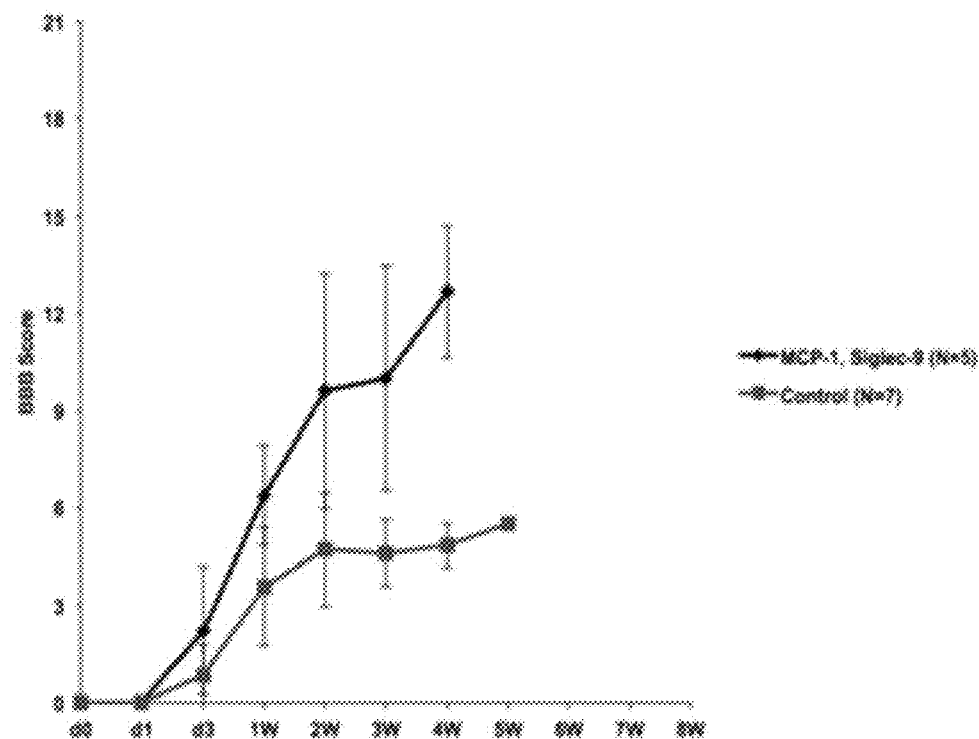
FIG. 10 shows elapsed time until functional recovery of hind legs after spinal cord contusion.

FIG. 10 shows progress over time in functional recovery of hind limbs after spinal cord contusion. Unlike the control rats, the MCP-1/ED-Siglec-9 administration rats exhibited a clear tendency towards early functional recovery. The data in the figure show average±SD.

(Interaction of ED-siglec-9 with the MCP-1 Receptor CCR2)

FIG. 11 shows results of immune precipitation, lectin blotting and Western blotting. ED-Siglec-9 interacted physically with sialylated CCR2 in THP-1 cell lysate, CSPG treatment caused an increase in microglial CCR2 expression, and ED-Siglec-9 interacted physically with microglial CCR2.

The physical interactions among the MCP-1 receptor, CCR2 and Ed-siglec-9 were analyzed using the human monocytic cell strain THP-1, which expresses abundant endogenous CCR2. As shown in FIG. 11(A), in SDS-PAGE analysis, the THP-1 cells expressed multiple CCR2 proteins with different molecular weights (FIG. 11(A) total lysate). Two important types of CCR2 proteins were detected at 55 and 42 kDa by immune precipitation of a THP-1 lysate using anti-CCR2 antibodies (FIG. 11(A) anti-CCR2). In particular, a sugar chain containing α2-3 binding sialic acid (a principal target of Siglec-9) was confirmed in MAH blotting. Moreover, only CCR2 proteins with large molecular weights were detected by MAH, and MAH was strongly reduced by sialidase treatment (FIG. 11(A) MAH-blot). Sialylated CCR2 proteins with large molecular weights were only detected in THP-1 lysate precipitated with ED-Siglec-9-Fc (FIG. 11(A) CCR2-blot). Pre-treatment of the THP-1 lysate with sialidase inhibited the physical interaction between CCR2 and ED-Siglec-9 (FIG. 11(A) CCR2-blot (sialidase+)). The physical interaction of ED-Siglec-9 and CCR2 was dependent on sialylated CCR2 containing α2-3 binding sialic acid.

In the case of the CSPG-treated native microglia, there was an increase in expression of CCR2 proteins with different molecular weights (FIG. 11(B)). CSPG contributed at least partially to inducing M2 by increasing expression of CCR2. Even in the native microglia, moreover, sialylated CCR2 with a higher molecular weight was detected in microglial lysate precipitated with ED-Siglec-9. ED-Siglec-9 was shown to interact physically with mouse microglial sialylated CCR2.

Example 3

Application to Acute Lung Damage (Interstitial Pneumonia)

In this example, it was discovered that inflammation and fibrosis accompanying acute lung damage were suppressed by administration of MCP-1 and ED-Siglec-9.

(Acute Lung Damage Model Mouse)

Bleomycin (BLM), which causes damage to alveolar epithelial cells, was dissolved 3 mg/ml in PBS to prepare a PBS solution of BLM. This solution was administered intratracheally at a level of 6 U/kg to 7 to 9 week old C57Bl/6J mice, and after 24 hours the presence of lung damage was confirmed by listening to Velcro rale.

Figures 12A, 12B:
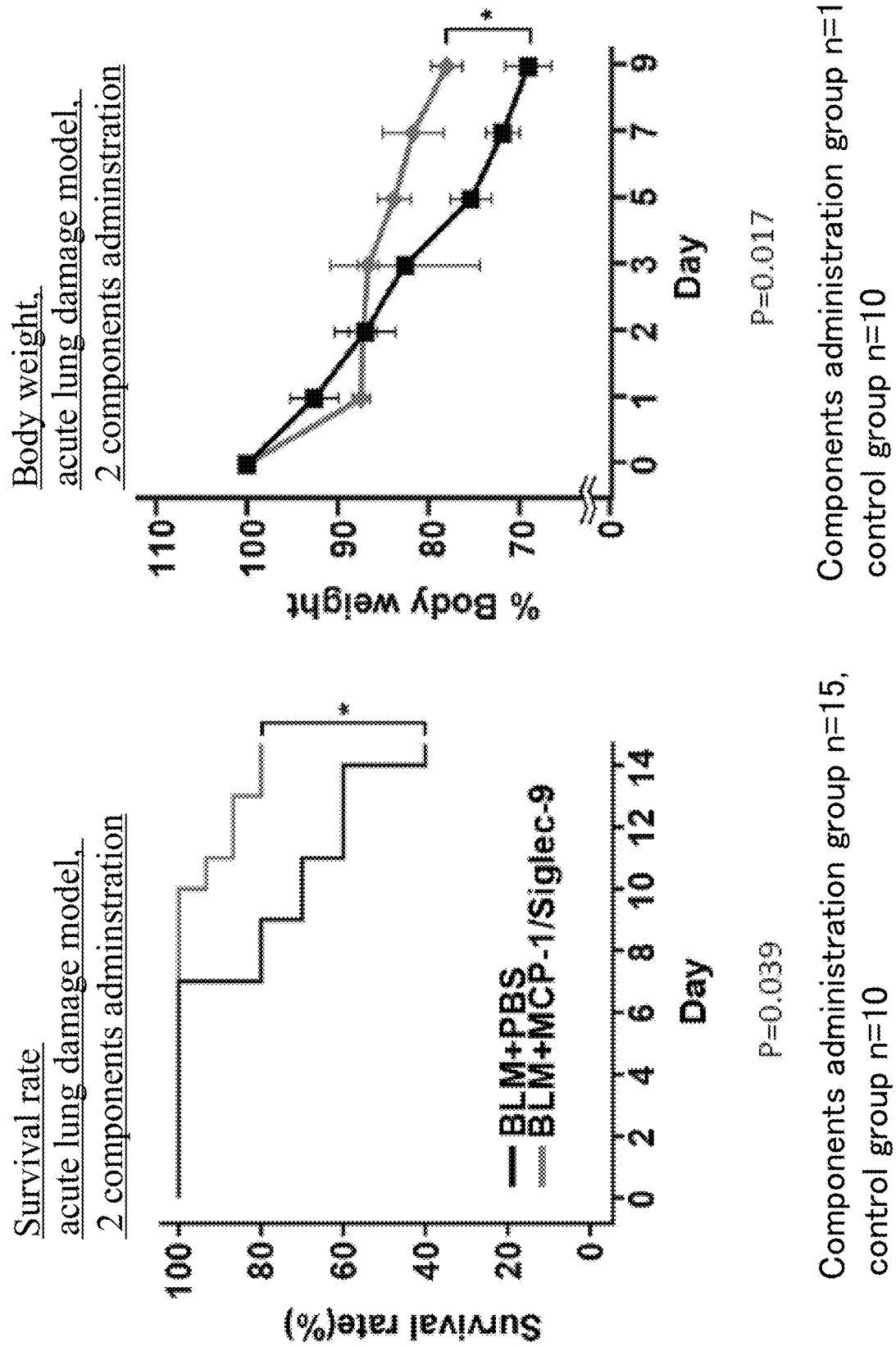
FIGS. 12A and 12B shows changes in survival rates and body weights in a MCP-1/ED-Siglec-9 administration group and a non-administration (PBS administration) group.

24 hours after lung damage, a PBS solution containing 1 μg/ml each of MCP-1 and ED-Siglec-9 recombinant protein was administered intravenously to the jugular veins of model mice, and the subsequent pathology was observed. FIG. 12 shows survival rates and weight changes in the MCP-1/ED-Siglec-9 administration group and non-administration (PBS administration) group.

(Evaluation of 9-Day Weight Ratios and 14-Day Survival Rates)

As shown in FIG. 12, in the C57Bl/6J mice in the PBS administration group with lung damage caused by intratracheal administration of the BLM solution (6 U/kg), the 9-day weight ratio fell to 70% (n=10), and the 14-day survival rate fell to about 40% (n=10).

In the MCP-1/ED-Siglec-9 administration group, on the other hand, the 9-day weight ratio remained at about 80% (n=15), and the 14-day survival rate was about 80% (n=15), confirming a reduction in lung damage.

(Pathological Analysis of Lung Damage Model)

Advanced fibrosis and breakdown of alveolar structure are observed in the lungs of lung damage patients. Because the lungs of model mice with damage caused by BLM exhibit similar structural changes, these structural changes and increases in collagenous fibers were evaluated by HE staining and Masson trichrome (MT) staining. The results are shown in FIG. 13.

Figure 13:
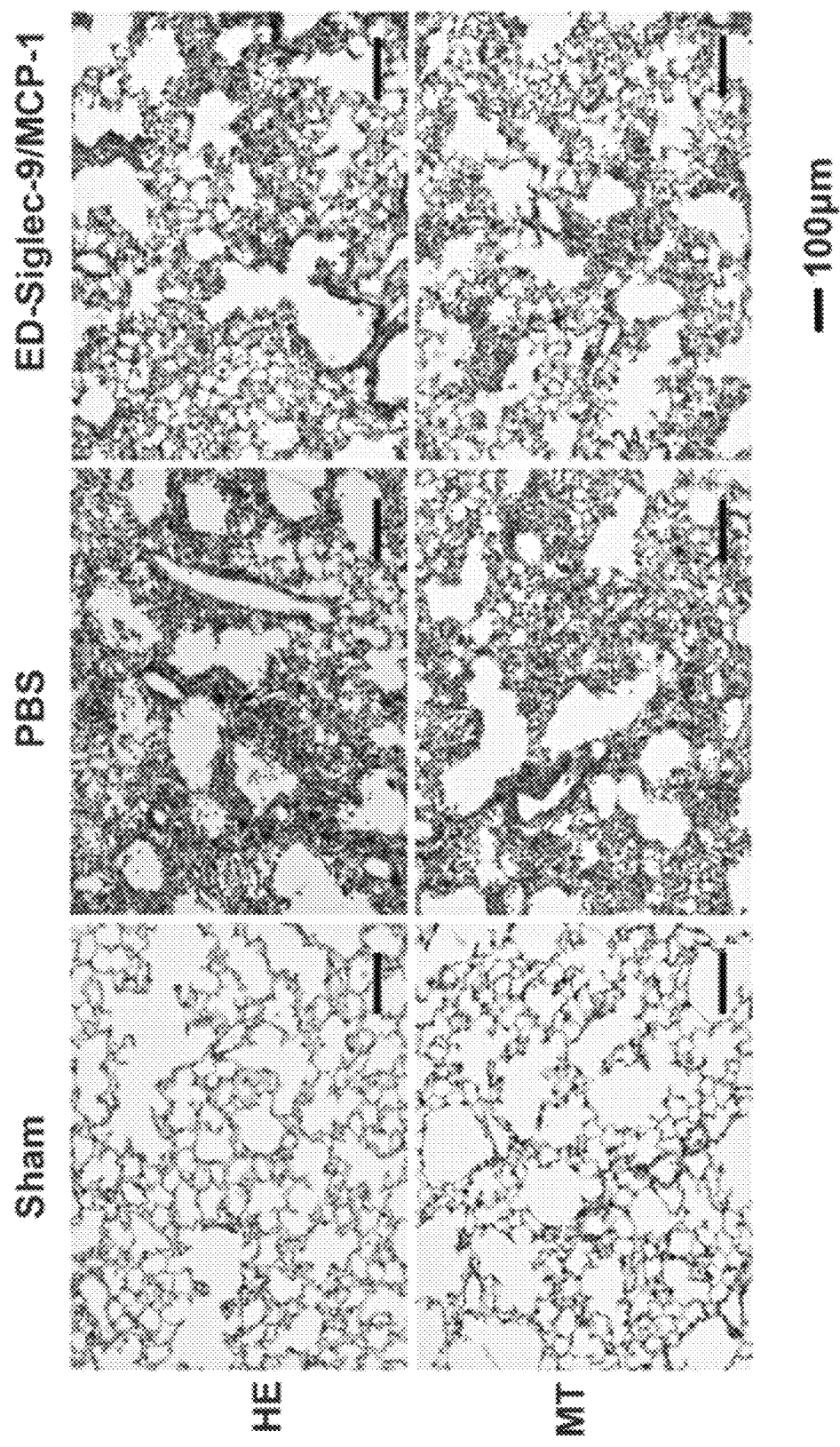
FIG. 13 shows results for structural changes and increases in collagen fiber in lung tissue, as evaluated by HE staining and Masson trichrome (MT) staining.

As shown in FIG. 13, obvious fibrosis and breakdown of the alveolar structures were observed in the non-administration group 7 days after BLM administration, but in the MCP-1/ED-siglec-9 administration group fibrosis was suppressed, and the alveolar structures appeared more close to normal (n=5).

These results show that administration of MCP-1 and ED-Siglec-9 has a repairing effect even on tissue damage caused by inflammatory disease in the lungs, and thus is effective for treating or preventing pulmonary fibrosis and other inflammatory lung disorders and acute lung disorders.

Example 4

Application to Hepatic Cirrhosis (Chronic Hepatitis)

In this example, it was discovered that hepatic cirrhosis and chronic hepatitis are resolved by MCP-1/ED-Siglec-9 administration.

(Preparation of Hepatic Cirrhosis Model Mice)

Carbon tetrachloride ($CCl_4$) was dissolved at a concentration of 1.0 ml/kg in olive oil to prepare a drug for inducing liver damage. This solution was administered intraperitoneally twice a week for 4 weeks continuously to C57BL6 mice (20 to 25 g) to prepare hepatic cirrhosis model mice. Recombinant protein ED-Siglec-9 and MCP-1 were dissolved at concentrations of 1 μg/ml in PBS to prepare a mixed solution for the model mice. 500 μl of this mixed solution was administered intravenously once 24 hours after the final $CCl_4$ solution administration (1 month after the start of $CCl_4$ administration), and clinical improvements were verified.

(Pathological Analysis of Hepatic Cirrhosis Model)

Figure 14:
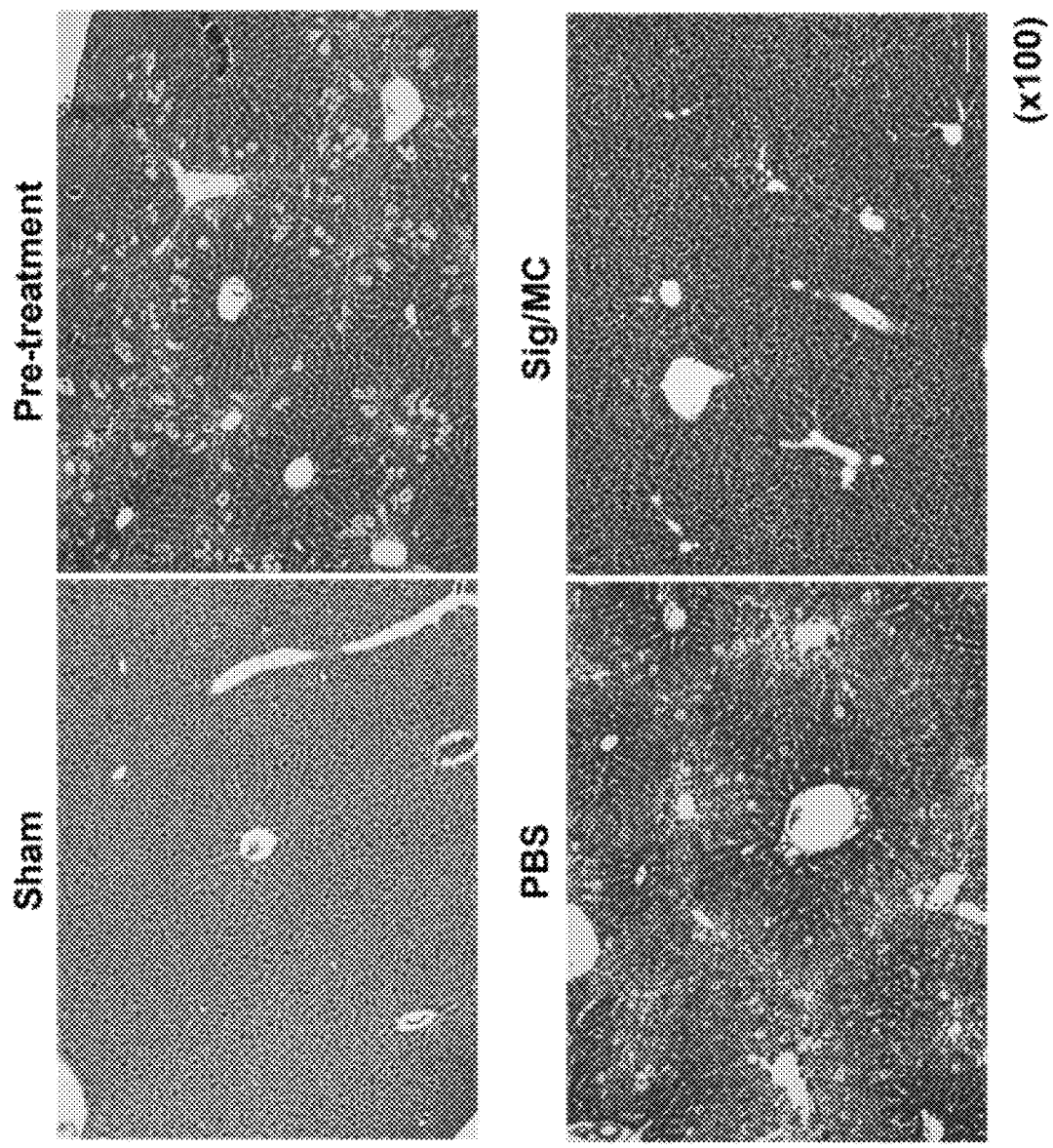
FIG. 14 shows the results of HE staining results of liver tissue in hepatic cirrhosis model mice.
Figure 15:
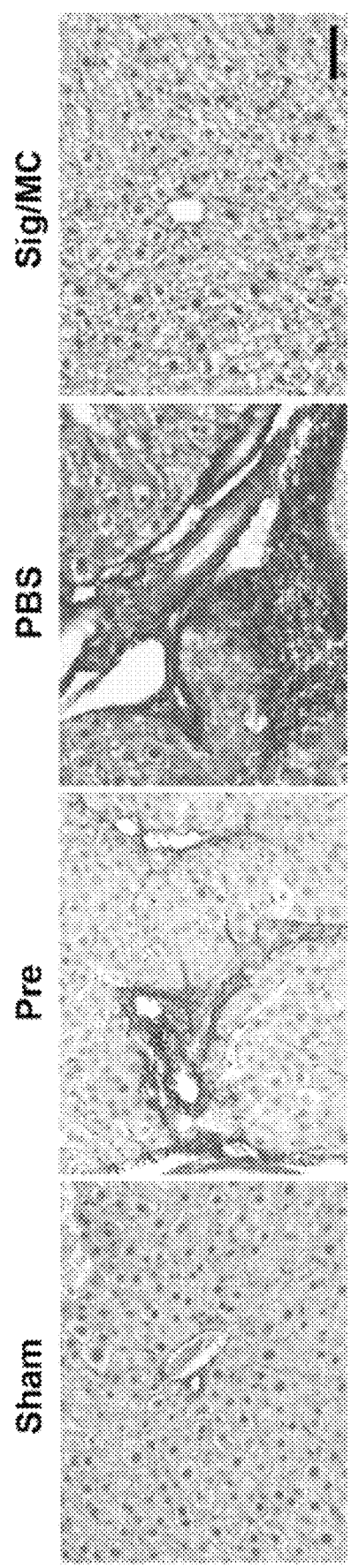
FIG. 15 shows the results of Sirius red staining (red stain for fibrin) of lung tissue in hepatic cirrhosis model mice.

Hepatic cell death, inflammatory cell infiltration and a widespread increase in irreversible fibrous tissue are observed in the livers of patients with hepatic cirrhosis and chronic hepatitis. 3 days after Ed-Siglec-9 and MCP-1 administration, a tissue analysis was performed on the ED-Siglec-9/MCP-1 administration group and the non-administration (PBS administration) group. FIGS. 14 and 15 respectively show the results of HE staining and Sirius red staining (red stain for collagen I).

As shown in FIG. 14, normal liver tissue was observed with Sham, but many dead liver cells and advanced fibrosis in the space of Disse were observed in the pre-treatment tissue (immediately before ED-siglec-9/MCP-1 administration). Severe cell infiltration and obvious fibrosis were observed in the PBS administration group, but the tissue images from the ED-Siglec-9/MCP-1 administration group appeared similar to normal liver tissue.

Moreover, as shown in FIG. 15, the results of Sirius red staining confirmed severe fibrosis in the pre-treatment and PBS administration groups. On the other hand, almost no fibrosis was confirmed in the ED-Siglec-9/MCP-1 administration group.

(Genetic Analysis of Hepatic Cirrhosis and Chronic Hepatitis Model)

RNA was extracted from liver tissue 3 days after ED-Siglec-9/MCP-1 administration, and expression of inflammatory cytokines and other genes was analyzed by quantitative PCR. The results are shown in FIGS. 16 and 17.

Figure 16:
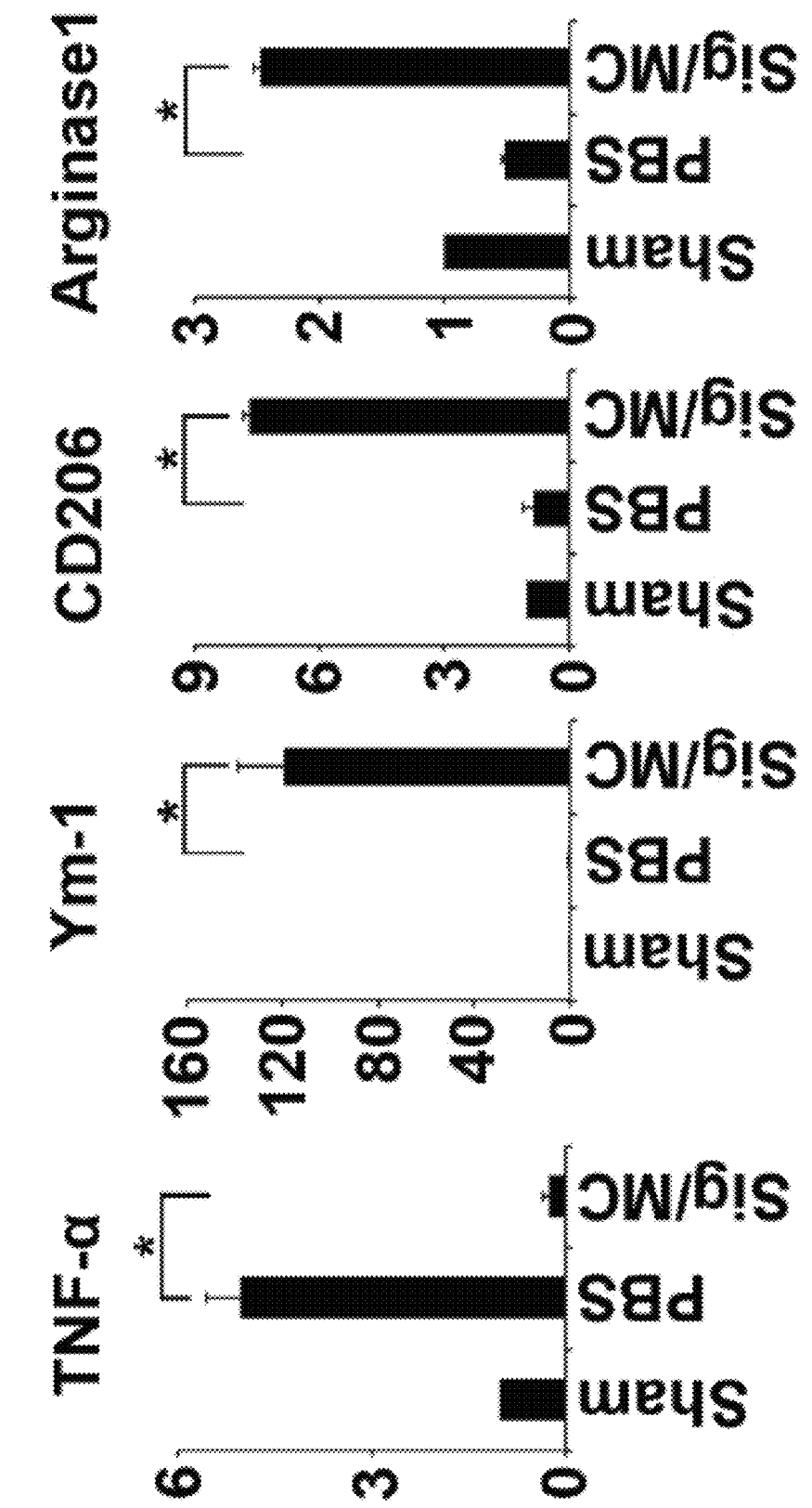
FIG. 16 shows the results of a quantitative PCR analysis of gene expression of inflammatory cytokines and the like in liver tissue 3 days after ED-Siglec-9/MCP-1 administration.

As shown in FIG. 16, while expression of TNF-α (produced by inflammation-promoting M1 macrophages) increased in the PBS administration group, TNF-α expression was suppressed in the ED-siglec-9/MCP-1 administration group, while expression of the anti-inflammatory M2 macrophage markers Ym-1, CD206 and Arginase-1 increased.

Figure 17:
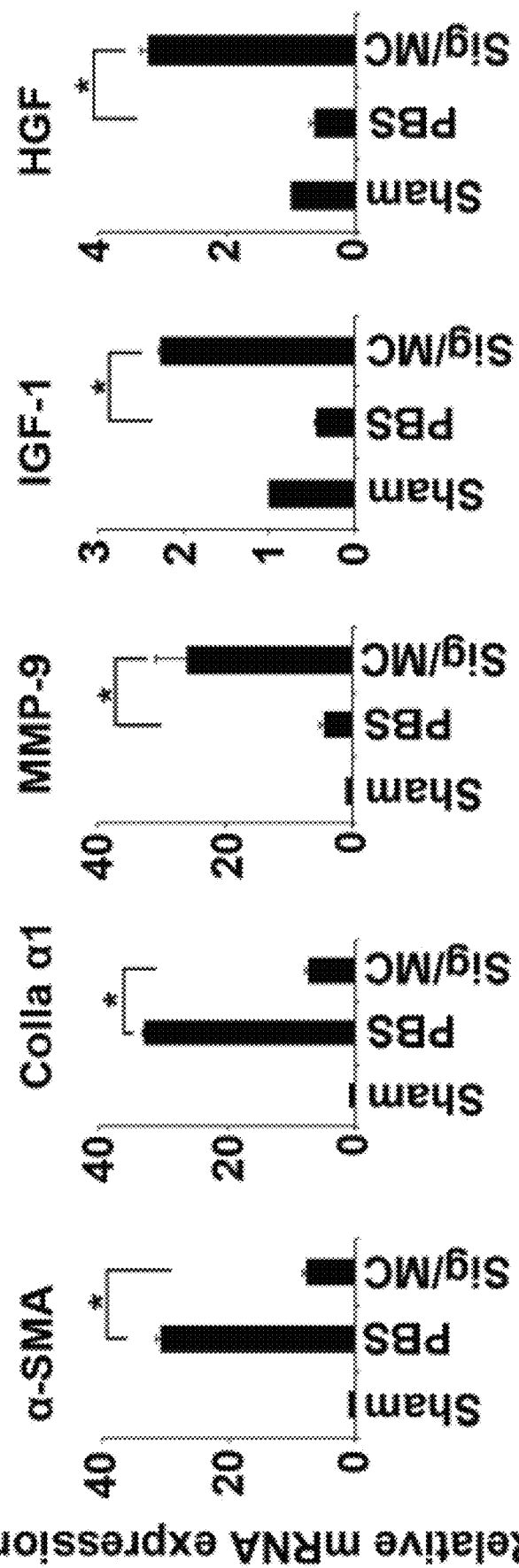
FIG. 17 shows the results of a quantitative PCR analysis of gene expression of inflammatory cytokines and the like in liver tissue 3 days after ED-Siglec-9/MCP-1 administration.

Moreover, as shown in FIG. 17, expression of collagen α1 and α-smooth muscle actin (α-SMA) (produced by activated hepatic stellate cells) increased in the PBS administration group. However, α-SMA expression was suppressed in the ED-siglec-9/MCP-1 administration group. At the same time, increases were observed in the expression levels of factors associated with liver regeneration, such as matrix metalloproteinase-9 (MMP-9, associated with fibrolysis), IGF-1, HGF and the like.

(Staining for Activated Hepatic Stellate Cell Marker α-SMA)

Liver tissue collected from the ED-Siglec-9 and MCP-1 administration group and the non-administration (PBS administration) group was stained for α-SMA. The results are shown in FIG. 18.

Figure 18:
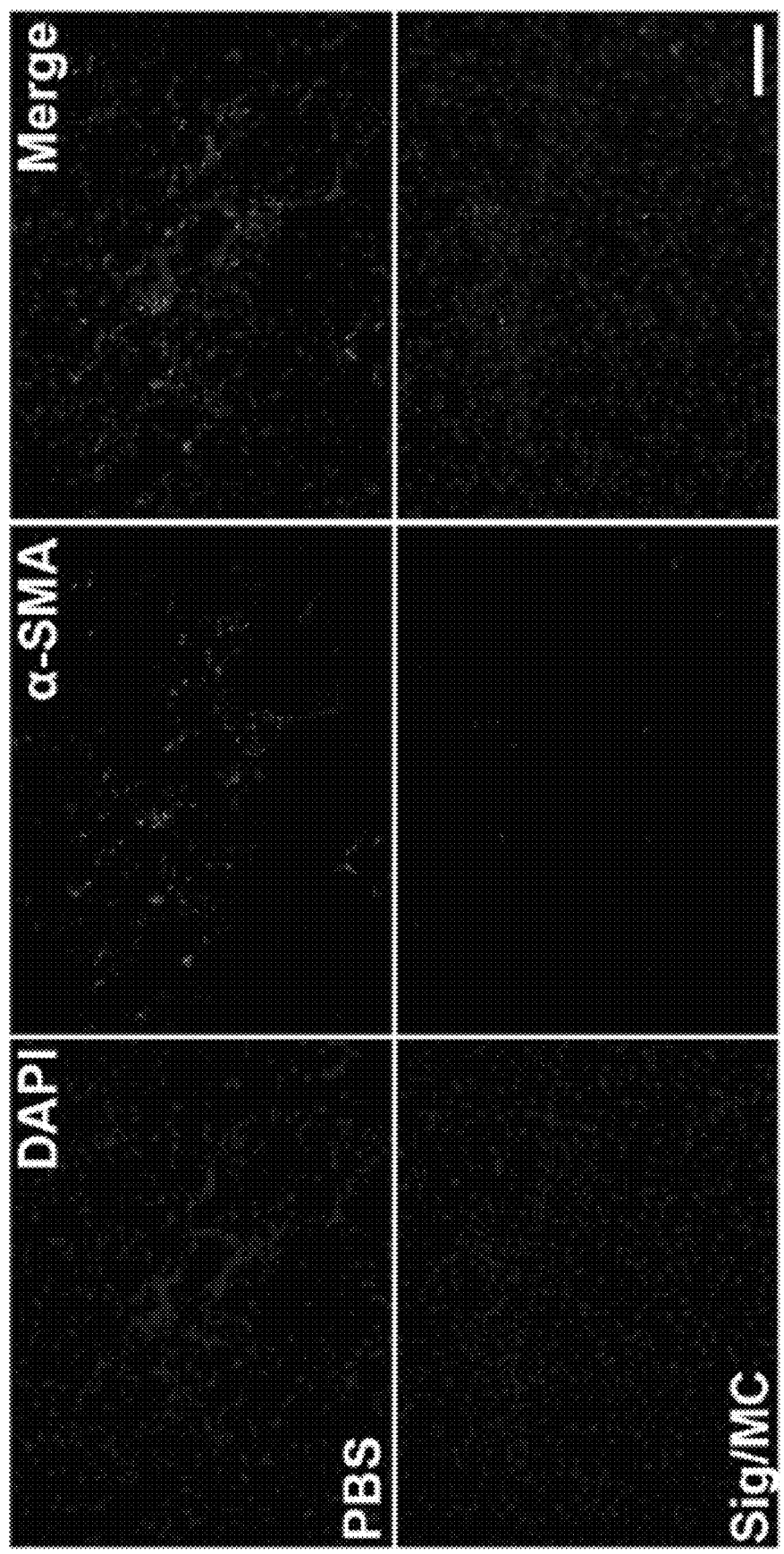
FIG. 18 shows the results of α-SMA staining in liver tissue collected from a ED-Siglec-9/MCP-1 administration group and non-administration (PBS administration) group.

As shown in FIG. 18, the number of α-SMA-positive cells was reduced in the ED-siglec-9/MCP-1 administration group.

From this it can be seen that hepatic cell death, inflammatory cell infiltration and increases in irreversible fibrous tissue that are specific to cirrhosis can be suppressed by administering ED-Siglec-9 and MCP-1 to livers with cirrhosis.

Example 5

In this example it was discovered that autoimmune arthritis is dramatically improved by intravenous administration of ED-Siglec-9, and the site of action appears to rest in the autoimmune system itself.

(Analysis of Therapeutic Usefulness Using Collagen-Induced Arthritis Model Mice)

(Preparation of Collage-Induced Arthritis Model Mice)

Figure 19:
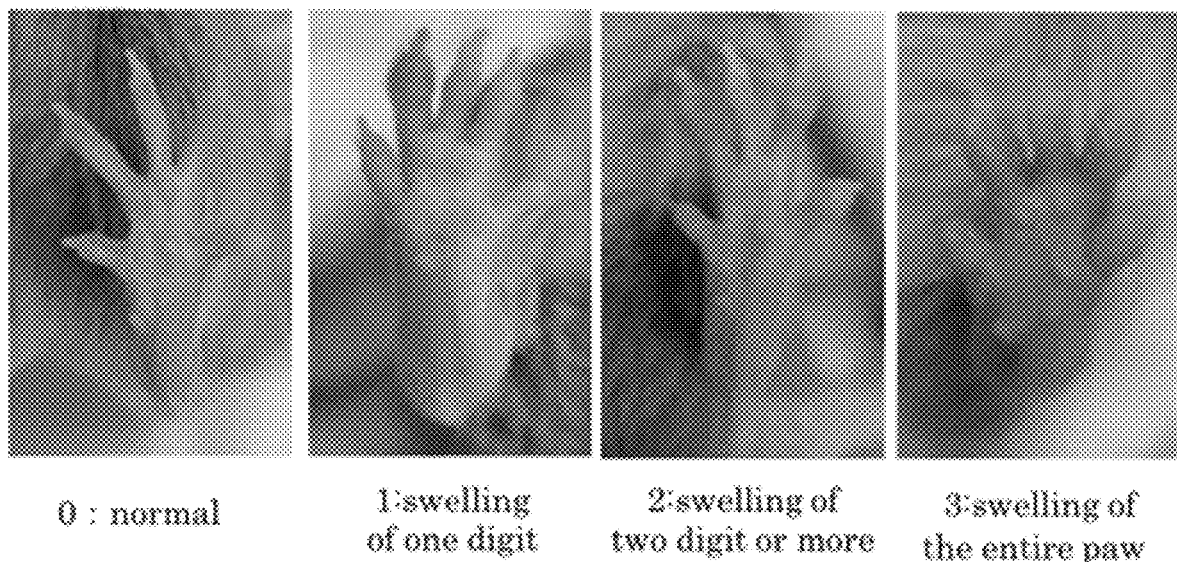
FIG. 19 shows the evaluation standard for an arthritis score showing severity of arthritis.

Mice with collagen-induced arthritis are used as an important animal model of rheumatoid arthritis. Type 2 collagen from an animal of a different species (cow) was administered subcutaneously at the base of the tails of DBA/1J mice, and then administered again 21 days later to cause collage-induced arthritis. The severity of the arthritis was evaluated using an arthritis score. Using the scoring system shown in FIG. 19, the average arthritis score of each group were calculated. Each mouse with an arthritis score of 1 or greater was considered to have arthritis.

(1) Analysis of Arthritis Suppression Effects of ED-Siglec-9 Administration in Collagen-Induced Arthritis (CIA) Mice First, four groups (each n=7) including a control group (saline) and three ED-siglec-9 groups (0.1 μg, 1 μg and 10 μg/mouse) were studied to determine the optimum dose of ED-siglec-9. Two days after the second collagen administration, saline or a concentration of ED-Siglec-9 was administered through the jugular vein, and the arthritis scores were evaluated 7 days later. The results are shown in FIG. 20.

Figure 20A:
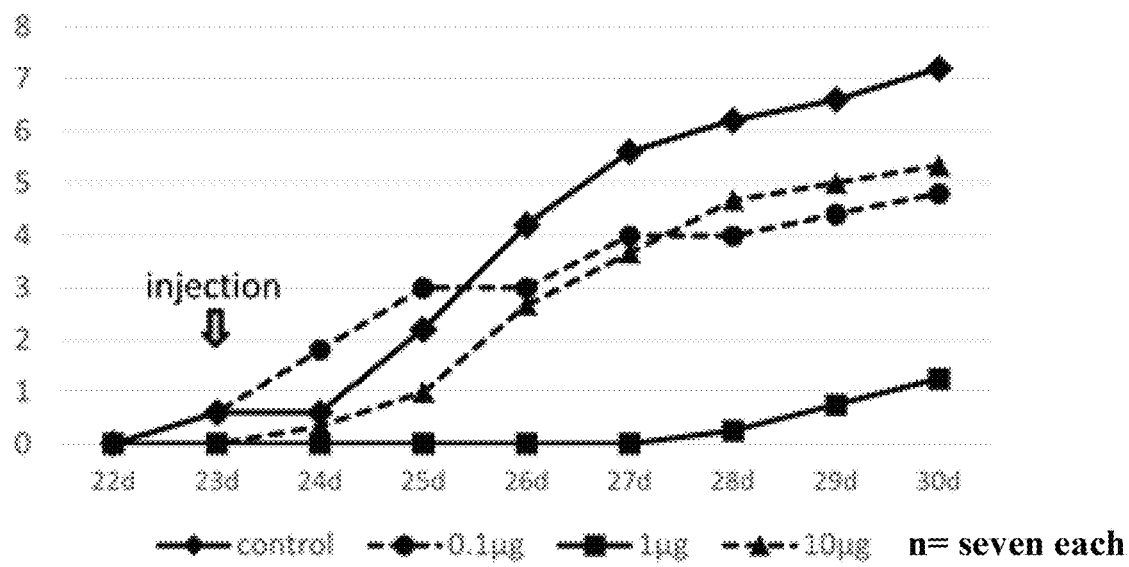
FIGS. 20A and 20B shows analysis results for arthritis suppression effects from ED-Siglec-9 administration in CIA mice.
Figure 20B:
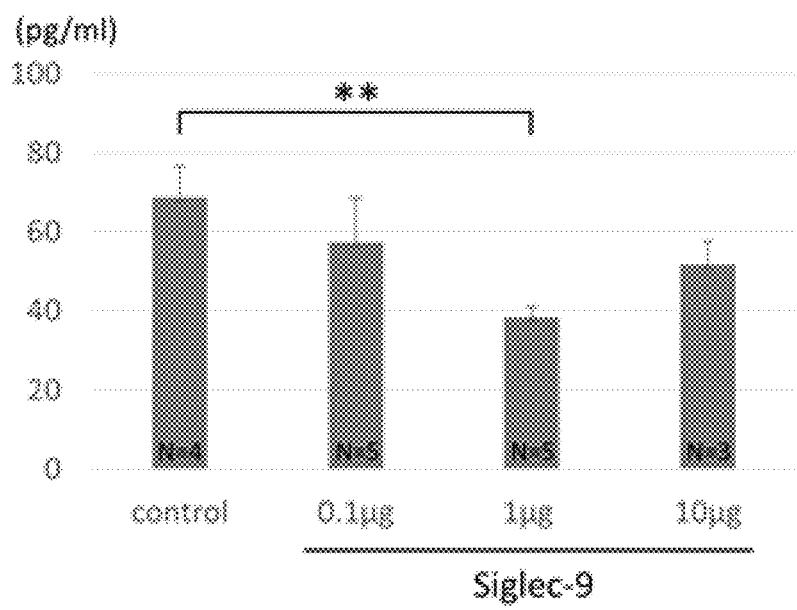

As shown in FIG. 20, the 0.1 and 10 μg ED-Siglec-9 administration groups were not significantly different from the control group, but the 1 μg group had significantly lower arthritis scores than the control group. The serum concentrations of TNF-α, which is an important inflammatory cytokine in rheumatoid arthritis, were measured at the same time, and were found to be significantly lower in the 1 μg group than in the control group.

Next, the long-term arthritis suppression effects of repeated administration of ED-Siglec-9 were investigated. The dose of ED-Siglec-9 was set at 1 μg. Beginning two days after the second collagen administration, saline or ED-siglec-9 was administered through the jugular veins once every 7 days. The arthritis score evaluation results are shown in FIG. 21.

As shown in FIG. 21, while the incidence of arthritis had reached 100% in the control group by the time of the final evaluation, the incidence was significantly lowered to 40% in the ED-Siglec-9 administration group. The arthritis scores were also significantly lower, averaging 4.33 in the control group and 1.4 in the ED-Siglec-9 group. The correlation between serum TNF-α concentrations and arthritis scores was also investigated at the same time in the ED-Siglec-9 administration group and control group, and an extremely significant correlation was found, with a correlation coefficient (R) of 0.837.

(Gene Expression Changes Caused by ED-Siglec-9 in Mouse Macrophages and Synovial Fibroblasts from Human Rheumatoid Arthritis)

The in vivo (CIA mouse) mechanism of action of the arthritis suppression effects of ED-Siglec-9 was investigated in vitro. In rheumatoid arthritis, inflammatory cytokines (TNF-α, etc.) secreted by activated immune cells (macrophages, etc.) stimulate the synovial cells, and the activated synovial cells secrete proteases (MMP-3, etc.), ultimately causing bone and cartilage damage. To discover whether the site of action of ED-Siglec-9 rests in the immune system or in the synovium (which is the main seat of inflammation), an experiment was performed using macrophages (a primary immune cell in autoimmune disorders) and synovial cells (a principal seat of inflammation).

Macrophages were isolated (n=4) from inside the abdominal cavities of DBA/1J mice. These were pre-treated for 1 hour with ED-Siglec-9 (5 to 20 ng/ml) and stimulated for 12 hours with LPS (0.2 μg/ml), after which mRNA was extracted and gene expression was measured by real-time PCR. The results are shown in FIG. 22(A).

Figure 22A:
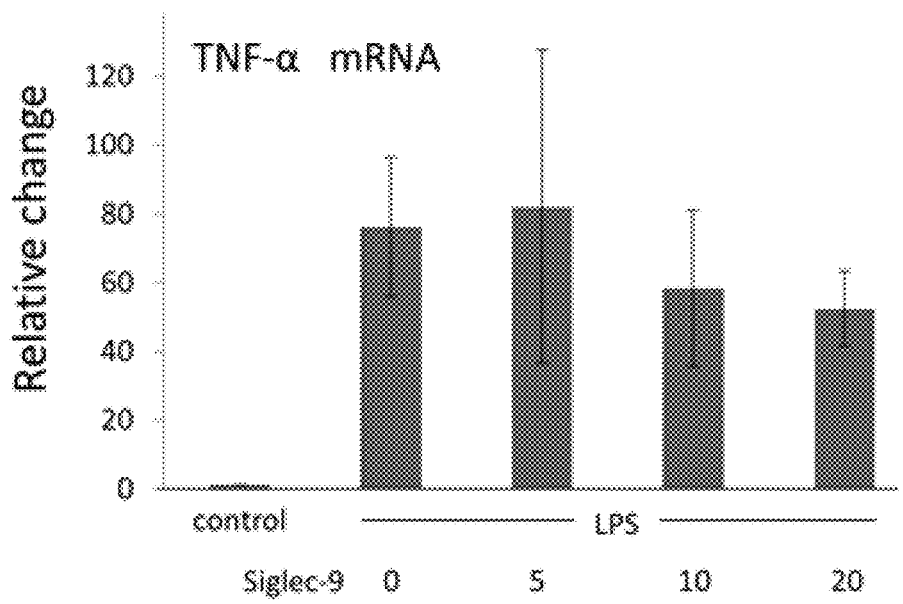

As shown in FIG. 22(A), ED-Siglec-9 tended to dose-dependently suppress increased expression of TNF-α (a typical inflammatory cytokine in rheumatoid arthritis) caused by LPS stimulus.

Next, an experiment was performed using synovial fibroblast (FLS) cells isolated enzymatically from synovial tissue collected from rheumatoid arthritis patients during artificial knee joint replacement surgery (n=3). The synovial fibroblasts were cultured for 48 hours and stimulated for 12 hours with TNF-α (10 mg/ml) with or without ED-Siglec-9 (50 ng/ml), after which mRNA was extracted and gene expression was measured by real-time PCR. The results are shown in FIG. 22(B).

Figure 22B:
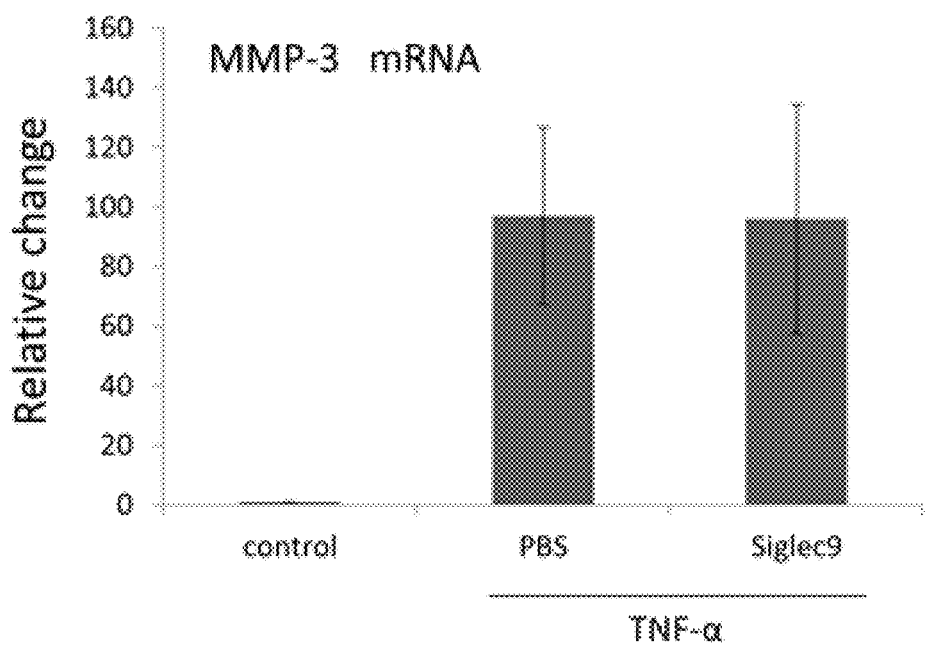
FIG. 22B shows that ED-Siglec-9 administration has no obvious suppression effect on increased expression of MMP-3 caused by TNF-α in synovial fibroblasts from human rheumatoid arthritis.

As shown in FIG. 22(B), ED-Siglec-9 had no obvious suppression effect on increased expression of MMP-3 (a typical protease produced in synovitis) caused by TNF-α in synovial fibroblasts from human rheumatoid arthritis.

These results suggest that the site of action of ED-siglec-9 in CIA mice rests not in its anti-inflammatory effects on local synovitis, but in the autoimmune system itself, which is attributable to the occurrence and development of autoimmune arthritis.

Example 6

It has become obvious that the balance of inflammatory/tissue-destroying M1 macrophages and anti-inflammatory/tissue-regenerating M2 macrophages plays an important role in building a tissue-regenerating environment. In acute and chronic inflammation, unregulated M1-macrophage activation promotes widespread fibrosis of tissue injury, preventing tissue repair. On the other hand, anti-inflammatory M2-macrophagees promote tissue repair by encouraging revascularization, phagocytosis of dead cells, and growth and aggregation of stem cells in the body. However, the M2 induction ability of the body is limited, and M1 predominates in most tissue damage environments. It has been discovered that ED-Siglec-9 and MCP-1 covert M1-centered inflammatory tissue damage environments into anti-inflammatory environments of tissue regeneration.

(Rat Skull Loss Model: Morphological Analysis)

The scalp and periosteum of a 7-week-old SD rat were peeled back under general or local anesthesia, and skull was removed under irrigation with a 5 mm diameter bone-collecting trephine bur to form a bone defect. The periosteum was preserved. ED-Siglec-9 and MCP-1 (100 ng each) were dissolved in PBS, atelocollagen was implanted in the bone loss site as a scaffold, and the skin was replaced and sutured to close the wound. 6 weeks after surgery μCT and a histological evaluation (H-E stain) were performed. The results are shown in FIG. 23.

Figure 23:
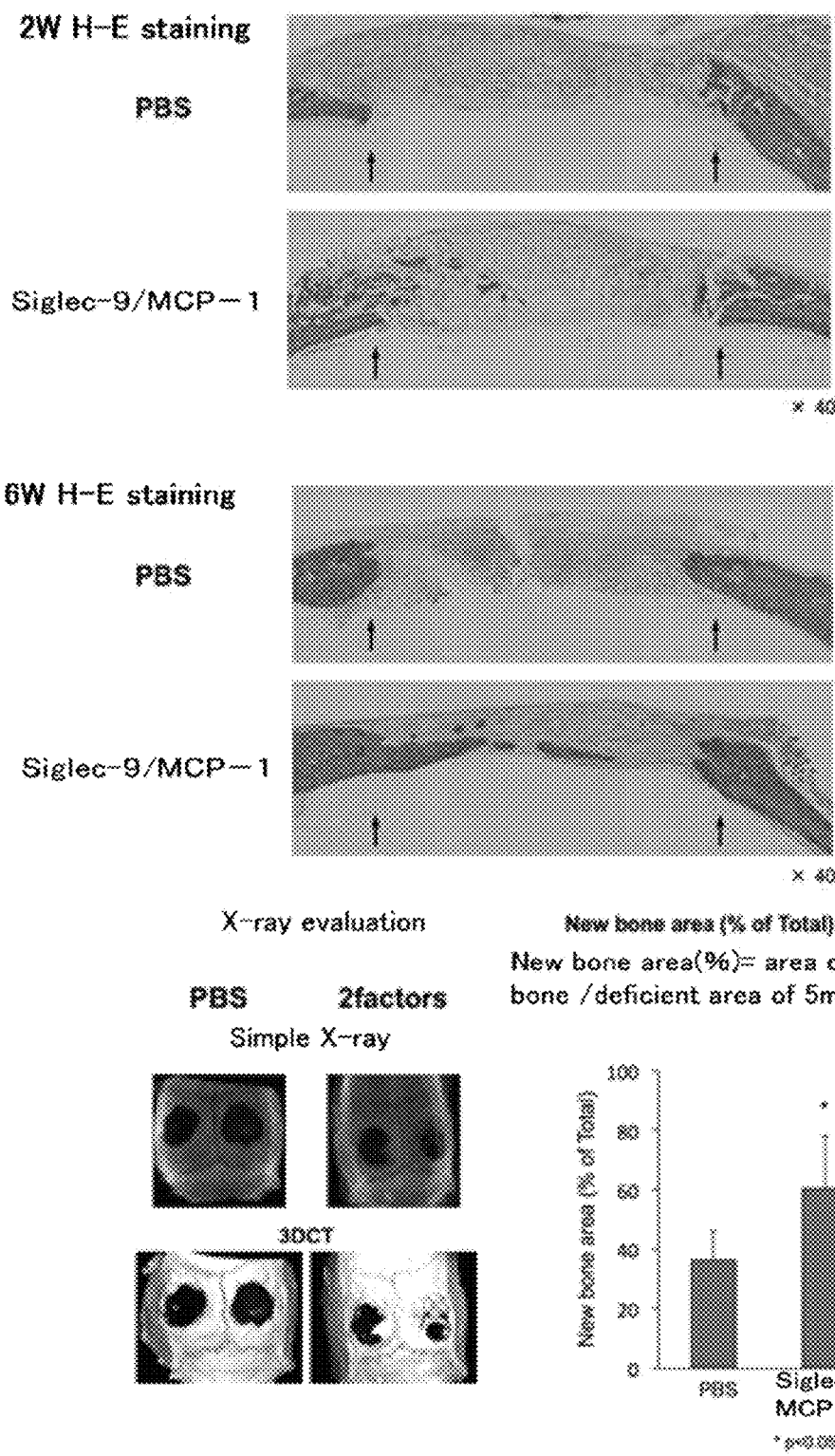
FIG. 23 illustrates bone regeneration effects 6 weeks after ED-Siglec-9/MCP-1 administration in a rat skull defect model, showing H-E staining, micro-CT results and percentage of bone regeneration.

As shown in FIG. 23, obvious bone regenerating effects were confirmed both histologically and in the CT 6 weeks after surgery when ED-Siglec-9/MCP-1 was administered to a rat skull loss model. These results show that ED-Siglec-9/MCP-1 is clinically applicable as a preparation of factors for promoting bone regeneration.

Example 7

In this example, a glucose-responsive insulin secretion test was performed. MIN6 ($1 \times 10^6$/well) cells were cultured to 90% confluence, and washed 3 times with DMEM (serum-free culture liquid). The culture liquid was replaced with SHED-CM and SHED-CM with various added antibodies (anti-human IgG: 1/500, anti-human ED-Siglec-9 antibody: 1/500, anti-MCP-1 antibody: 1/500, anti-human ED-siglec-9 antibody: 1/500+anti-MCP-1 antibody: 1/500), and cultured for 6 hours. Next, the cells were starved for 30 minutes in low-glucose KRB buffer (2.5 mM), and then stimulated for 30 minutes with low-glucose KRB buffer (2.5 mM) and high-glucose KRB buffer (16.7 mM). After stimulus the supernatant was collected, after which the insulin content was collected with acid ethanol. The amount of insulin in the supernatant (release) and the insulin content after supernatant collection (content) were measured by the HTRF (trademark) method, and insulin secretion ability was compared by comparing the release/content (%) ratio. The results are shown in FIG. 24.

Figure 24:
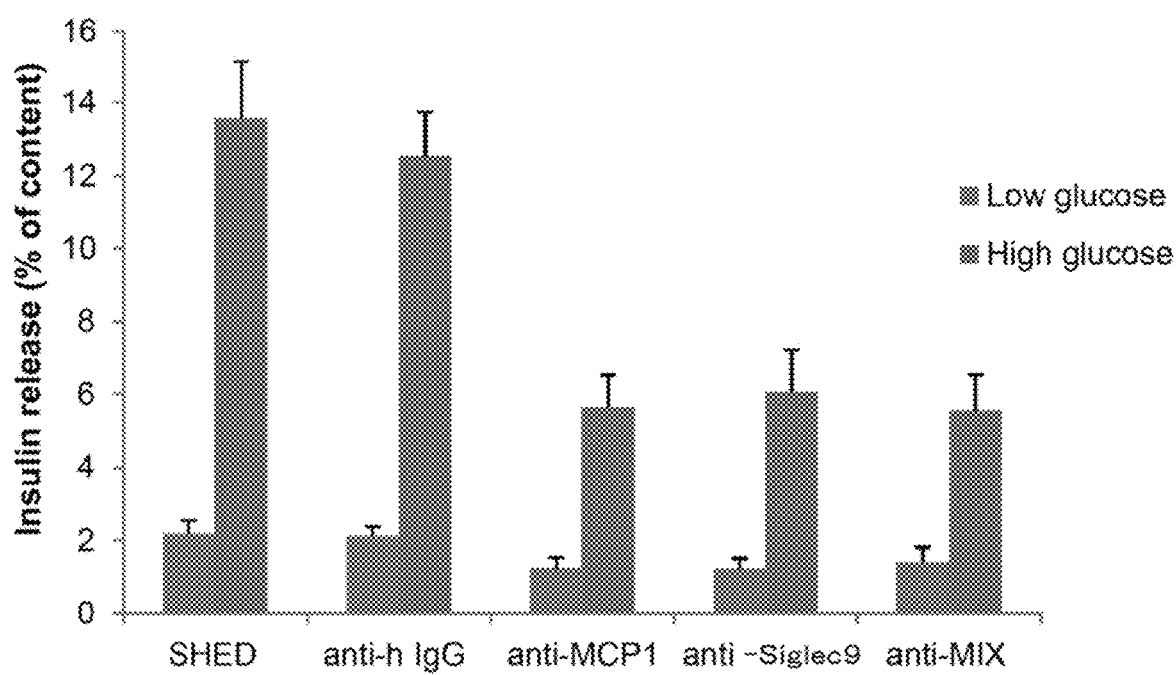
FIG. 24 shows the results of a comparative study of insulin secretion ability using MIN cells.

As shown in FIG. 24, when the factors were blocked with neutral antibodies, insulin secretion ability declined significantly in comparison with the SHED-CM results when using anti-ED-Siglec-9, anti-MCP-1 and anti-MIX (ED-Siglec-9+MCP-1). Since no decline in insulin producing ability occurred with the control (IgG), it appears that ED-siglec-9 and MCP-1 contribute to insulin secretion by pancreatic β-cells.

SEQUENCE LISTING FREE TEXT

SEQ ID NOS:7 to 36: primers

The invention claimed is:

1. A method of treating a disease selected from the group consisting of hepatitis, severe hepatitis, hepatic cirrhosis, interstitial pneumonia, spinal cord injury, and an autoimmune disease, comprising administering to a subject in need thereof a component comprising an extracellular domain activity of sialic acid-binding immunoglobulin-type lectin-9 (Siglec-9), the component not having a cytoplasmic domain of Siglec-9.

2. The method according to claim 1, wherein the disease is an autoimmune disease selected from the group consisting of rheumatoid arthritis, multiple sclerosis, type I diabetes, Sjogren's syndrome, and systemic erythematosus.

3. The method according to claim 1, wherein the disease is selected from the group consisting of hepatitis, severe hepatitis, hepatic cirrhosis, interstitial pneumonia, rheumatoid arthritis, and spinal cord injury.

4. The method according to claim 1, wherein the disease is rheumatoid arthritis.

5. The method according to claim 1, wherein the component comprises an extracellular domain of Siglec-9.

6. The method according to claim 5, wherein the component does not comprise a transmembrane domain of Siglec-9.

7. The method according to claim 5, wherein the extracellular domain of Siglec-9 has an amino acid sequence having 90% or more identity with the amino acid sequence represented by SEQ ID NO: 4.

8. The method according to claim 5, wherein the extracellular domain of Siglec-9 has the amino acid sequence represented by SEQ ID NO: 4.

9. The method according to claim 1, wherein the component comprises an amino acid sequence having 90% or more identity with the amino acid sequence represented by SEQ ID NO: 4.

10. The method according to claim 9, wherein the component comprising an extracellular domain activity of Siglec-9 comprises an extracellular domain of Siglec-9 and the component comprising an MCP-1 activity is MCP-1.

11. The method according to claim 1, wherein the method further comprises administering to the subject a component comprising a monocyte chemotactic protein-1 (MCP-1) activity.

12. The method according to claim 11, wherein the component comprising an MCP-1 activity is MCP-1.

13. The method according to claim 12, wherein MCP-1 has an amino acid sequence having 90% or more identity with the amino acid sequence represented by SEQ ID NO: 2.

14. The method according to claim 12, wherein MCP-1 has the amino acid sequence represented by SEQ ID NO: 2.

15. The method according to claim 11, wherein the component comprising an MCP-1 activity comprises an amino acid sequence having 90% or more identity with the amino acid sequence represented by SEQ ID NO: 2.

16. The method according to claim 11, wherein the method further comprises administering to the subject at least one of chondroitin sulfate or chondroitin sulfate proteoglycan.

17. The method according to claim 11, wherein the component comprising an extracellular domain activity of Siglec-9 and the component comprising a MCP-1 activity are administered simultaneously.

18. The method according to claim 11, wherein the component comprising an extracellular domain activity of Siglec-9 and the component comprising a MCP-1 activity are administered successively.

19. The method according to claim 1, wherein the method further comprises administering to the subject at least one of chondroitin sulfate or chondroitin sulfate proteoglycan.

* * * * *